United States Patent
Richardson et al.

(10) Patent No.: US 7,455,646 B2
(45) Date of Patent: *Nov. 25, 2008

(54) POLYMER COATED GUIDE WIRE

(75) Inventors: Mark T. Richardson, Escondido, CA (US); David M. Anderson, Temecula, CA (US); Emmanuel C. Biagtan, Temecula, CA (US); Lawrence E. Brennan, Temecula, CA (US); David H. Burkett, Temecula, CA (US); Wayne E. Cornish, Fallbrook, CA (US); Robert C. Esselstein, Fallbrook, CA (US); James Jacobs, Mountain View, CA (US); Marc M. Jalisi, Temecula, CA (US); Daryush P. Mirzaee, Sunnyvale, CA (US); Olin J. Palmer, Mountain View, CA (US); John Schreiner, Hemet, CA (US); Kent C. Stalker, San Marcos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/768,794

(22) Filed: Jun. 26, 2007

(65) Prior Publication Data

US 2007/0249964 A1     Oct. 25, 2007

Related U.S. Application Data

(60) Division of application No. 10/631,275, filed on Jul. 31, 2003, which is a division of application No. 09/441,698, filed on Nov. 16, 1999, now Pat. No. 6,673,025, which is a continuation-in-part of application No. 09/203,140, filed on Dec. 1, 1998, now Pat. No. 6,390,993, which is a continuation-in-part of application No. 08/868,764, filed on Jun. 4, 1997, now abandoned.

(51) Int. Cl.
    *A61B 5/00*   (2006.01)
    *A61M 25/00*  (2006.01)
(52) U.S. Cl. ...................................... 600/585
(58) Field of Classification Search ............... 600/585
    See application file for complete search history.

(56) References Cited

U.S. PATENT DOCUMENTS 1,878,671 A    9/1932   Cantor
(Continued)

FOREIGN PATENT DOCUMENTS

DE    19728337 A1    7/1999
(Continued)

OTHER PUBLICATIONS

Athlete Plus, Guide Wire, Catalog No. 1 (Aug. 1995).
(Continued)

*Primary Examiner*—Max Hindenburg
*Assistant Examiner*—Emily M Lloyd
(74) *Attorney, Agent, or Firm*—Paul Y. Feng; Fuldwider Patton LLP

(57) ABSTRACT

A guidewire or section thereof, that has a core member or the like with a plurality of contiguous tapered segments having taper angles that are configured to produce a linear change in stiffness over a longitudinal portion of the device. The device may also have a core section with a continuously changing taper angle to produce a curvilinear profile that is configured to produce a linear change in stiffness of the core over a longitudinal portion of the device. An embodiment has a plurality of radiopaque elements that may be intermittent, continuous or in the form of a helical ribbon for scaled measurement of intracorporeal structure under flouroscopic imaging. Another embodiment has at least one layer of polymer over the distal end of the device.

27 Claims, 23 Drawing Sheets

U.S. PATENT DOCUMENTS

| | | |
|---|---|---|
| 2,022,065 A | 11/1935 | Wappler |
| 2,047,535 A | 7/1936 | Wappler |
| 3,196,876 A | 7/1965 | Miller |
| 3,516,412 A | 6/1970 | Ackerman |
| 3,687,142 A | 8/1972 | Leibinzohn |
| 3,731,671 A | 5/1973 | Mageoh |
| 3,789,841 A | 2/1974 | Antoshkiw |
| 3,802,440 A | 4/1974 | Salem et al. |
| 3,841,308 A | 10/1974 | Tate |
| 3,867,945 A | 2/1975 | Long |
| 3,924,632 A | 12/1975 | Cook |
| 3,928,519 A | 12/1975 | Kashiyama et al. |
| 3,941,119 A | 3/1976 | Corrales |
| 3,973,556 A | 8/1976 | Fleischhacker et al. |
| 3,999,551 A | 12/1976 | Spitz et al. |
| 4,003,369 A | 1/1977 | Heilman et al. |
| 4,013,079 A | 3/1977 | Lindermann et al. |
| 4,020,829 A | 5/1977 | Wilson |
| 4,080,706 A | 3/1978 | Heilman et al. |
| 4,085,757 A | 4/1978 | Pevsner |
| 4,169,464 A | 10/1979 | Obrez |
| 4,195,637 A | 4/1980 | Gruntzig et al. |
| 4,204,528 A | 5/1980 | Termanini |
| 4,211,741 A | 7/1980 | Ostoich |
| 4,257,421 A | 3/1981 | Beal |
| 4,283,447 A | 8/1981 | Flynn |
| 4,306,566 A | 12/1981 | Sinko |
| 4,345,602 A | 8/1982 | Yoshimura et al. |
| 4,385,635 A | 5/1983 | Ruiz |
| 4,388,076 A | 6/1983 | Waters |
| 4,419,095 A | 12/1983 | Nebergall et al. |
| 4,425,919 A | 1/1984 | Alston, Jr. et al. |
| 4,456,017 A | 6/1984 | Miles |
| 4,464,176 A | 8/1984 | Wijayrathna |
| 4,504,268 A | 3/1985 | Herlitze |
| 4,531,943 A | 7/1985 | Van Tassel et al. |
| 4,534,363 A | 8/1985 | Gold |
| 4,538,622 A | 9/1985 | Samson et al. |
| 4,545,390 A | 10/1985 | Leary |
| 4,554,929 A | 11/1985 | Samson et al. |
| 4,563,181 A | 1/1986 | Wijayarathna et al. |
| 4,619,274 A | 10/1986 | Morrison |
| 4,643,194 A | 2/1987 | Fogarty |
| 4,665,906 A | 5/1987 | Jervis |
| 4,682,607 A | 7/1987 | Vaillancurt et al. |
| 4,690,175 A | 9/1987 | Ouchi et al. |
| 4,721,117 A | 1/1988 | Mar et al. |
| 4,748,986 A * | 6/1988 | Morrison et al. ............. 600/585 |
| 4,757,827 A | 7/1988 | Buchbinder et al. |
| 4,763,647 A | 8/1988 | Gambale |
| 4,779,628 A | 10/1988 | Machek |
| 4,798,598 A | 1/1989 | Bonello et al. |
| 4,813,434 A | 3/1989 | Buchbinder et al. |
| 4,815,478 A | 3/1989 | Buchbinder et al. |
| 4,841,976 A | 6/1989 | Packard et al. |
| 4,846,186 A | 7/1989 | Box et al. |
| 4,867,174 A | 9/1989 | Skribiski |
| 4,873,983 A | 10/1989 | Winters |
| 4,884,579 A | 12/1989 | Engelson |
| 4,895,168 A | 1/1990 | Machek |
| 4,917,102 A | 4/1990 | Miller et al. |
| 4,917,104 A | 4/1990 | Rebell |
| 4,922,924 A | 5/1990 | Gambale et al. |
| 4,925,445 A | 5/1990 | Sakamoto et al. |
| 4,932,419 A | 6/1990 | de Toledo |
| 4,934,380 A | 6/1990 | de Toledo |
| 4,955,384 A | 9/1990 | Taylor et al. |
| 4,955,862 A | 9/1990 | Sepetka |
| 4,991,602 A | 2/1991 | Amplatz et al. |
| 4,992,924 A | 2/1991 | Gousset et al. |
| 5,003,990 A | 4/1991 | Osypka |
| 5,061,273 A | 10/1991 | Yock |
| 5,061,395 A | 10/1991 | Meng |
| 5,063,935 A | 11/1991 | Gambale et al. |
| 5,065,769 A | 11/1991 | de Toledo |
| 5,069,217 A | 12/1991 | Fleischhacker, Jr. et al. |
| 5,069,226 A | 12/1991 | Yamauchi et al. |
| 5,084,022 A | 1/1992 | Claude |
| 5,084,151 A | 1/1992 | Vallana et al. |
| 5,095,915 A | 3/1992 | Engelson |
| 5,111,829 A | 5/1992 | de Toledo |
| 5,120,308 A | 6/1992 | Hess |
| 5,127,917 A | 7/1992 | Niederhauser et al. |
| 5,129,890 A | 7/1992 | Baes et al. |
| 5,135,503 A | 8/1992 | Abrams |
| 5,144,959 A | 9/1992 | Gambale et al. |
| 5,147,317 A | 9/1992 | Shank et al. |
| 5,171,383 A | 12/1992 | Sagaye et al. |
| 5,174,302 A | 12/1992 | Palmer |
| 5,176,149 A | 1/1993 | Grenouillet |
| 5,178,158 A | 1/1993 | de Toledo |
| 5,184,627 A | 2/1993 | de Toledo |
| 5,209,730 A | 5/1993 | Sullivan |
| 5,213,111 A | 5/1993 | Cook et al. |
| 5,217,026 A | 6/1993 | Stoy et al. |
| 5,226,423 A | 7/1993 | Tenerz et al. |
| 5,228,453 A | 7/1993 | Sepetka |
| 5,229,211 A | 7/1993 | Murayama et al. |
| 5,238,004 A | 8/1993 | Sahatjian et al. |
| 5,241,970 A | 9/1993 | Johlin, Jr. et al. |
| 5,246,009 A | 9/1993 | Adams |
| 5,253,653 A * | 10/1993 | Daigle et al. ................ 600/585 |
| 5,259,353 A | 11/1993 | Nakai et al. |
| 5,259,393 A | 11/1993 | Corso, Jr. et al. |
| 5,267,574 A | 12/1993 | Viera et al. |
| 5,303,714 A | 4/1994 | Abele et al. |
| 5,313,967 A | 5/1994 | Lieber et al. |
| 5,333,620 A | 8/1994 | Moutafis et al. |
| 5,341,818 A | 8/1994 | Abrams et al. |
| 5,345,945 A | 9/1994 | Hodgson et al. |
| 5,358,493 A | 10/1994 | Schweich, Jr. et al. |
| 5,368,048 A | 11/1994 | Stoy et al. |
| 5,372,144 A | 12/1994 | Mortier et al. |
| 5,379,779 A | 1/1995 | Rowland et al. |
| 5,380,307 A | 1/1995 | Chee et al. |
| 5,385,152 A * | 1/1995 | Abele et al. ................ 600/585 |
| 5,402,799 A | 4/1995 | Colon et al. |
| 5,404,887 A | 4/1995 | Prather |
| 5,406,960 A | 4/1995 | Corso, Jr. |
| 5,421,955 A | 6/1995 | Lau et al. |
| 5,433,200 A | 7/1995 | Fleischhacker, Jr. |
| 5,437,288 A | 8/1995 | Schwartz et al. |
| 5,443,455 A | 8/1995 | Hergenrother et al. |
| 5,452,726 A | 9/1995 | Burmeister et al. |
| 5,460,187 A | 10/1995 | Daigle et al. |
| 5,465,732 A | 11/1995 | Abele |
| 5,465,733 A | 11/1995 | Hinohara et al. |
| 5,479,938 A | 1/1996 | Weier |
| 5,497,783 A | 3/1996 | Urick et al. |
| 5,497,785 A | 3/1996 | Viera |
| 5,497,786 A | 3/1996 | Urick |
| 5,498,250 A | 3/1996 | Prather |
| 5,516,336 A | 5/1996 | McInnes et al. |
| 5,573,520 A | 11/1996 | Schwartz et al. |
| 5,606,979 A | 3/1997 | Hodgson |
| 5,606,981 A | 3/1997 | Tartacower et al. |
| 5,622,184 A | 4/1997 | Ashby et al. |
| 5,636,641 A | 6/1997 | Fariabi |
| 5,640,970 A | 6/1997 | Arenas |
| 5,666,969 A | 9/1997 | Urick et al. |
| 5,702,419 A | 12/1997 | Berry et al. |
| 5,706,826 A | 1/1998 | Schwager |
| 5,722,424 A | 3/1998 | Engelson |
| 5,746,701 A | 5/1998 | Noone |

| | | | |
|---|---|---|---|
| 5,749,837 A | 5/1998 | Palermo et al. | |
| 5,750,206 A | 5/1998 | Hergenrother et al. | |
| 5,772,424 A | 6/1998 | Nokelainen | |
| 5,772,609 A | 6/1998 | Nguyen et al. | |
| 5,807,279 A | 9/1998 | Viera | |
| 5,827,201 A | 10/1998 | Samson et al. | |
| 5,830,155 A | 11/1998 | Frechette et al. | |
| 5,836,892 A | 11/1998 | Lorenzo | |
| 5,836,893 A | 11/1998 | Urick | |
| 5,840,046 A | 11/1998 | Deem | |
| 5,865,767 A | 2/1999 | Frechette et al. | |
| 5,876,356 A | 3/1999 | Viera | |
| 5,885,227 A | 3/1999 | Finlayson | |
| 5,891,055 A | 4/1999 | Sauter | |
| 5,984,877 A | 11/1999 | Fleischhacker, Jr. | |
| 5,984,878 A | 11/1999 | Engelson | |
| 6,004,279 A * | 12/1999 | Crowley et al. | 600/585 |
| 6,059,738 A | 5/2000 | Stoltze et al. | |
| 6,390,993 B1 * | 5/2002 | Cornish et al. | 600/585 |
| 6,666,829 B2 * | 12/2003 | Cornish et al. | 600/585 |
| 6,673,025 B1 * | 1/2004 | Richardson et al. | 600/585 |

FOREIGN PATENT DOCUMENTS

| | | | |
|---|---|---|---|
| EP | 0377453 | A1 | 7/1990 |
| EP | 0395098 | A1 | 10/1990 |
| EP | 0407965 | A1 | 1/1991 |
| EP | 0480427 | A1 | 4/1992 |
| EP | 0597341 | A1 | 5/1994 |
| EP | 0661073 | A1 | 5/1995 |
| EP | 0763365 | A1 | 3/1996 |
| EP | 0744186 | A1 | 11/1996 |
| EP | 0818215 | A1 | 1/1998 |
| JP | 8257136 | A6 | 10/1996 |
| WO | 9308862 | A1 | 5/1993 |
| WO | 9820810 | A1 | 5/1998 |
| WO | 9855173 | A1 | 12/1998 |
| WO | 9946109 | A1 | 9/1999 |
| WO | 0032265 | A1 | 6/2000 |
| WO | 0101888 | A1 | 1/2001 |

OTHER PUBLICATIONS

Choice Guidewires, SciMed Life Systems, Inc., Cardiology Issue vol. 1 (Feb. 1997).
Publication No. 08257136, Patent Abstracts of Japan, 1997 vol. 2 (Feb. 1997).
ACS Hi-Torque Ruler Guide Wire, Guidant Corporation (Apr. 1997).
Shinobi Guidewires, Cordis Corporation (Dec. 1997).
Luge Guide Wire, SciMed Life Systems, Inc. (Feb. 1998).

* cited by examiner

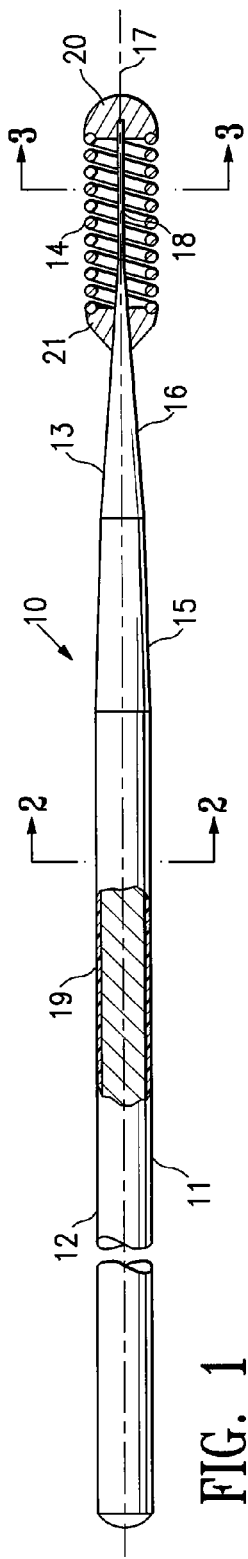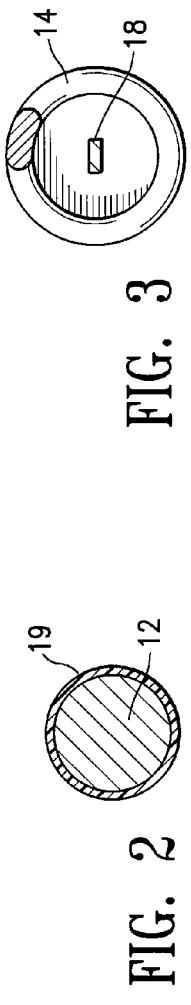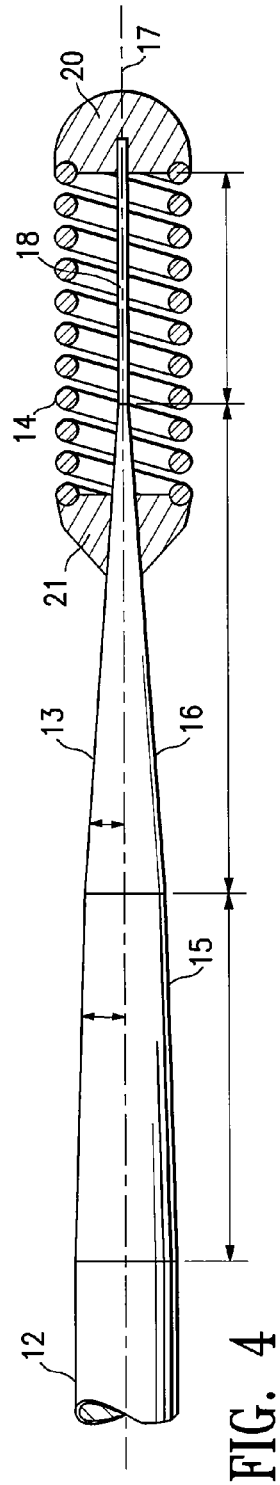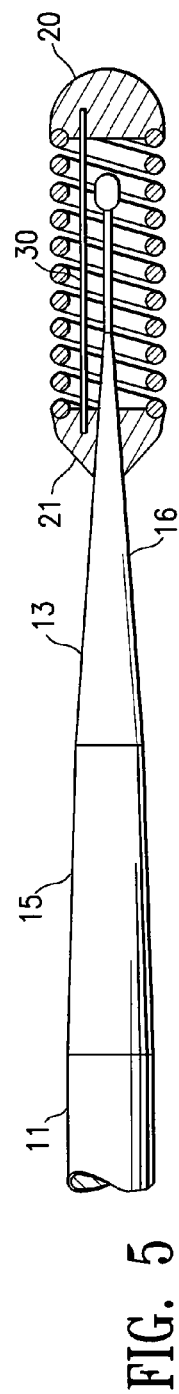
FIG. 1  FIG. 2  FIG. 3  FIG. 4  FIG. 5

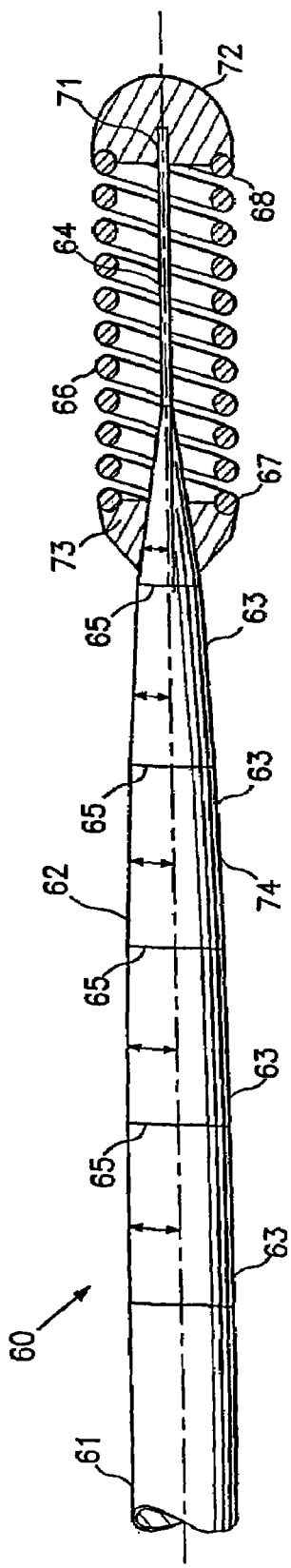
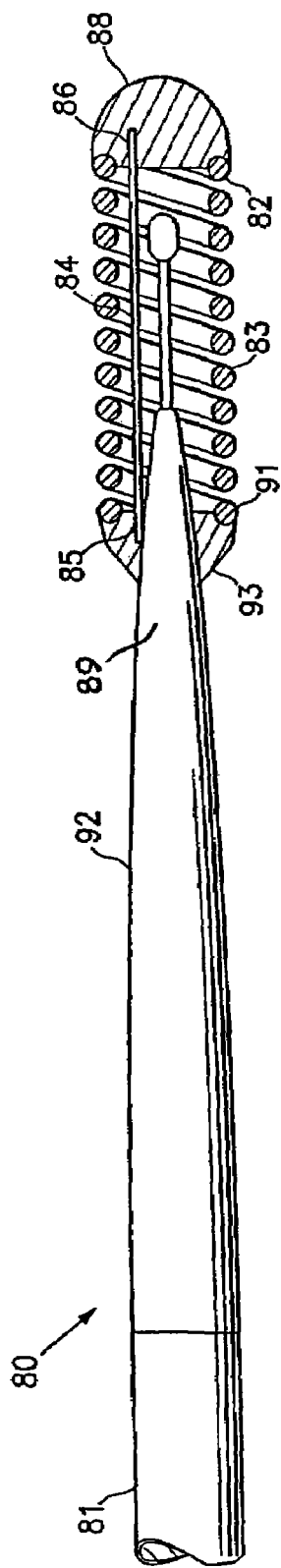
FIG. 9
FIG. 10

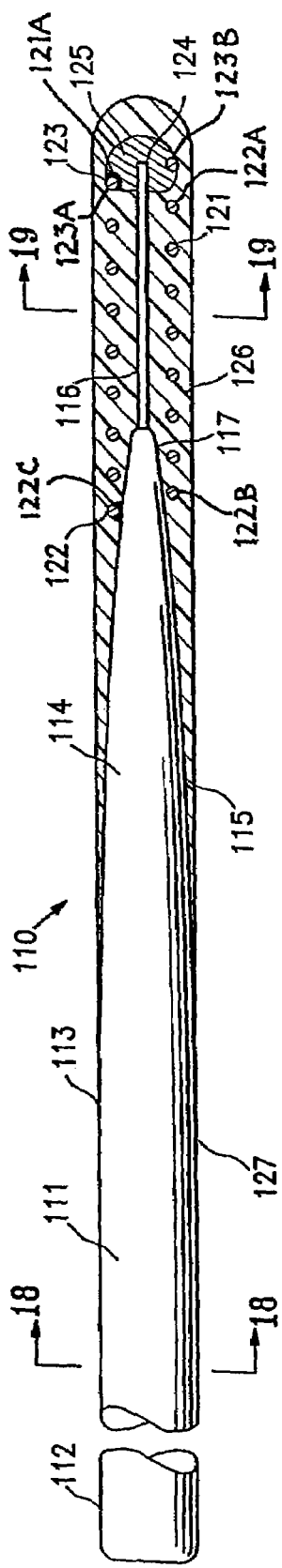
FIG. 17
FIG. 18
FIG. 19

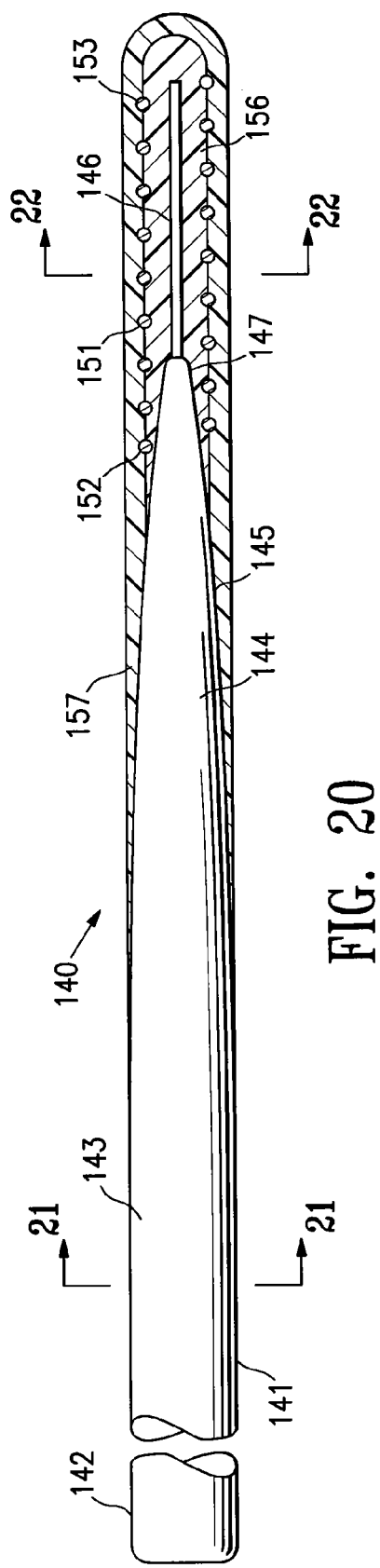

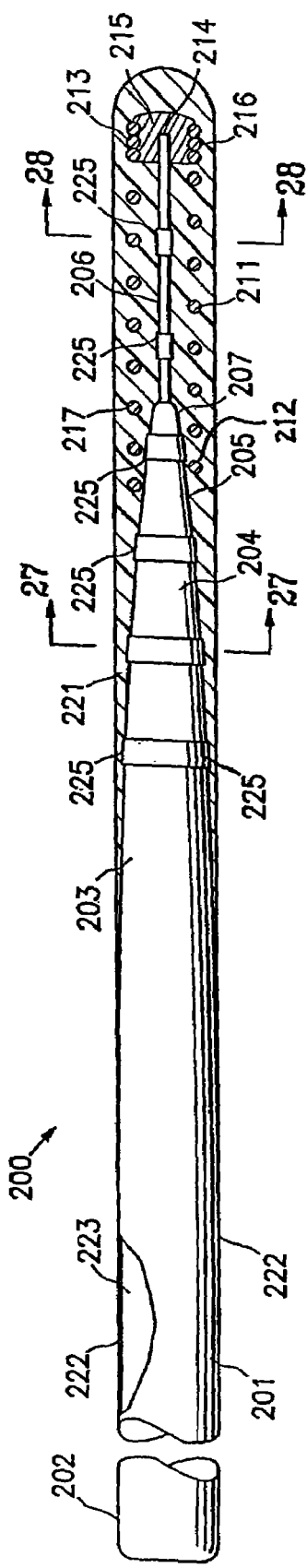
FIG. 26
FIG. 28
FIG. 27

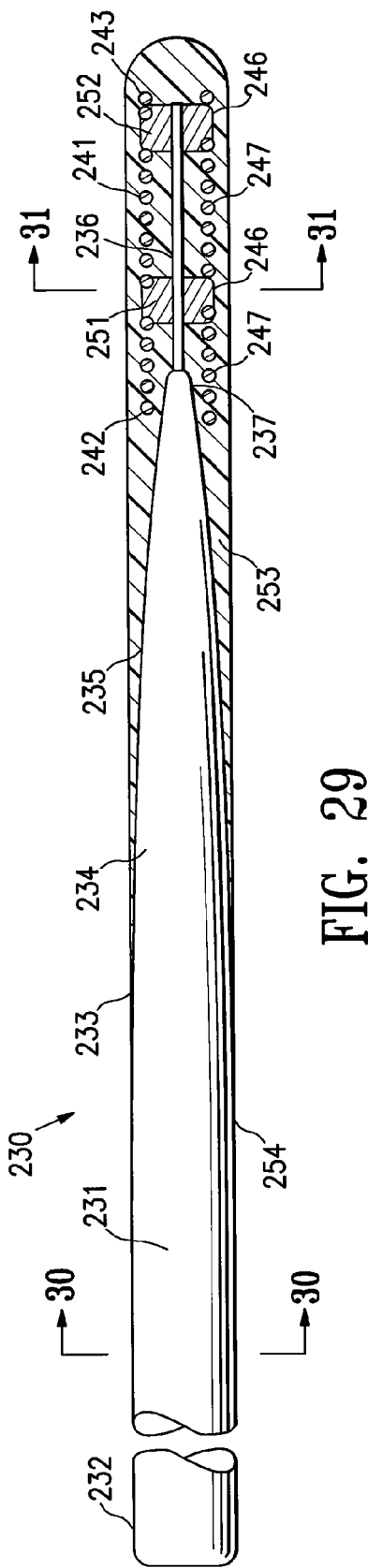
FIG. 29
FIG. 31
FIG. 30

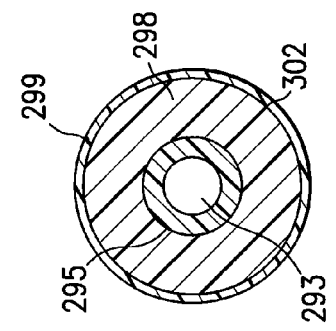
FIG. 38
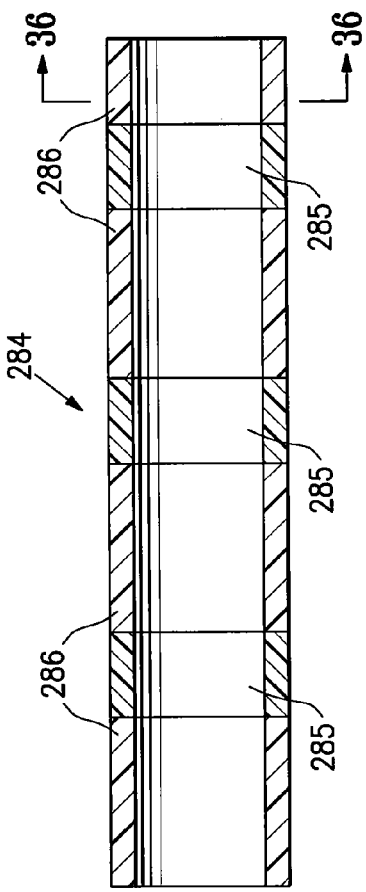
FIG. 35
FIG. 36
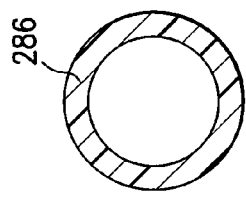
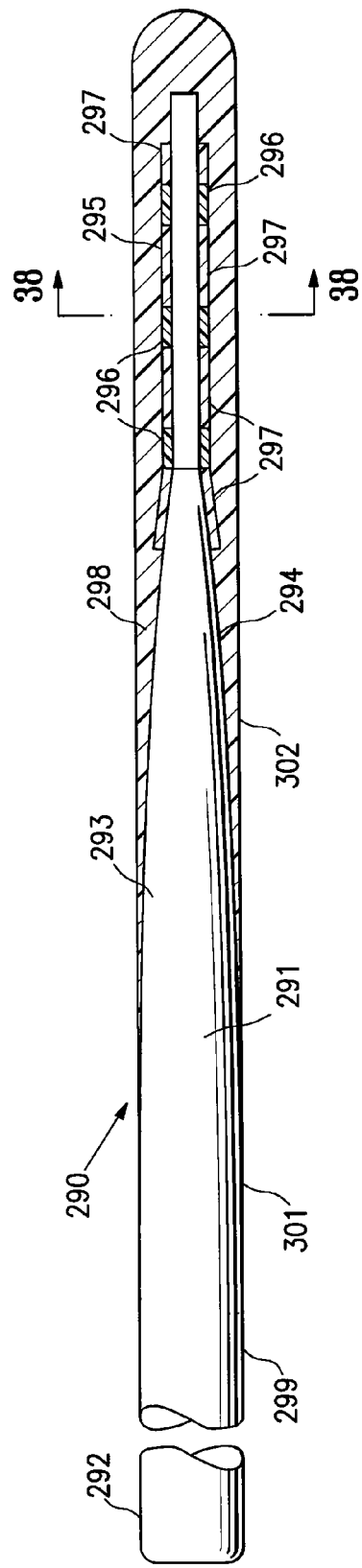
FIG. 37

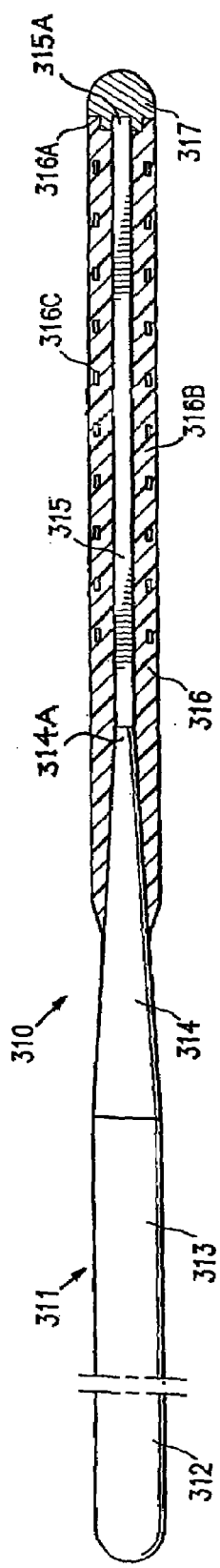
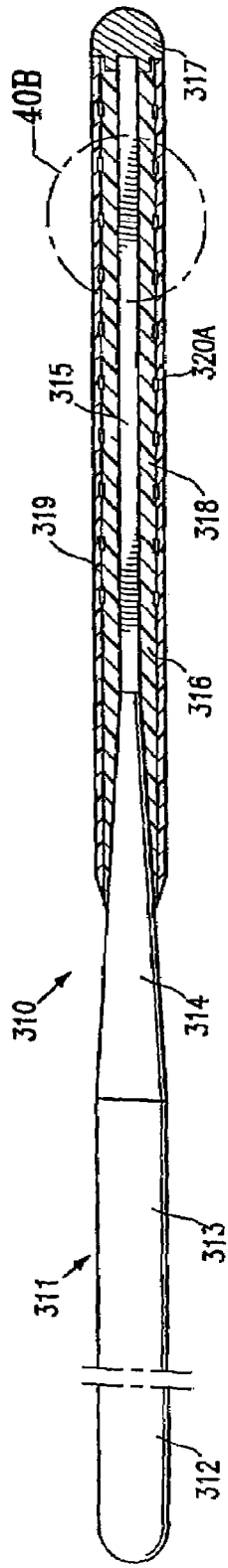
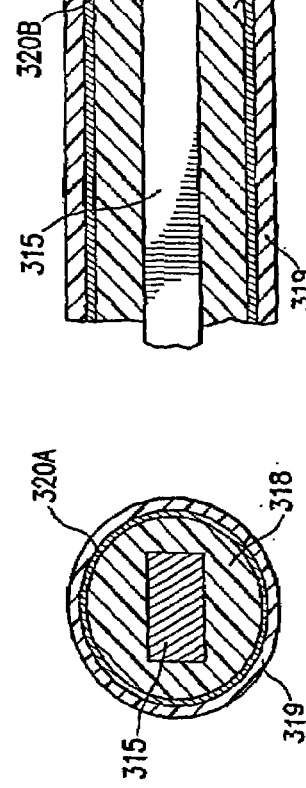
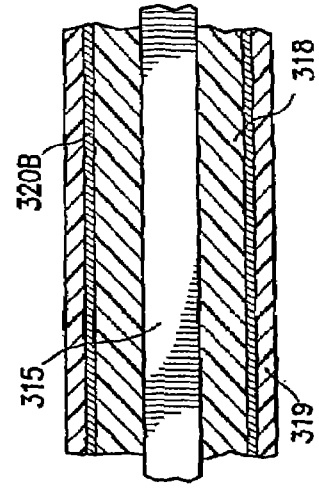
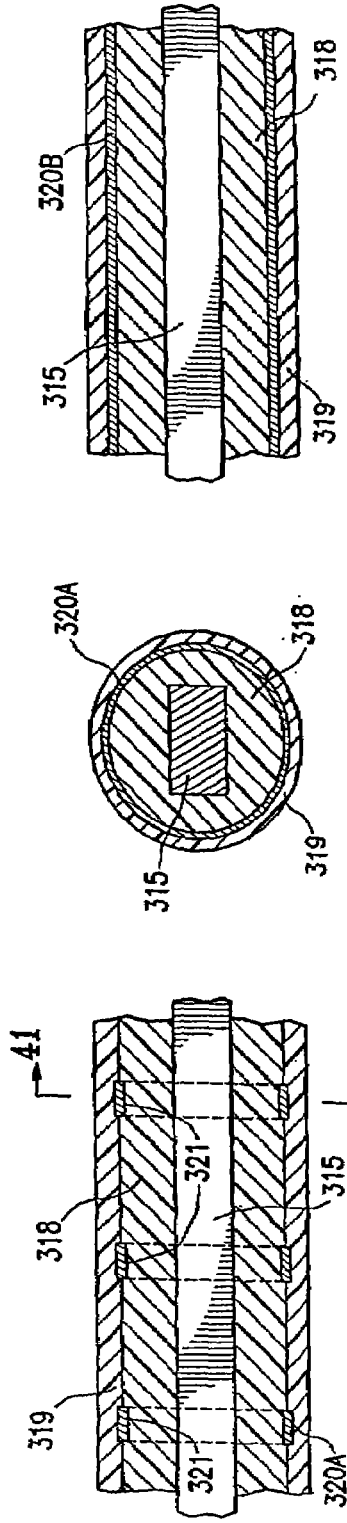
FIG. 39
FIG. 40A
FIG. 42
FIG. 41
FIG. 40B

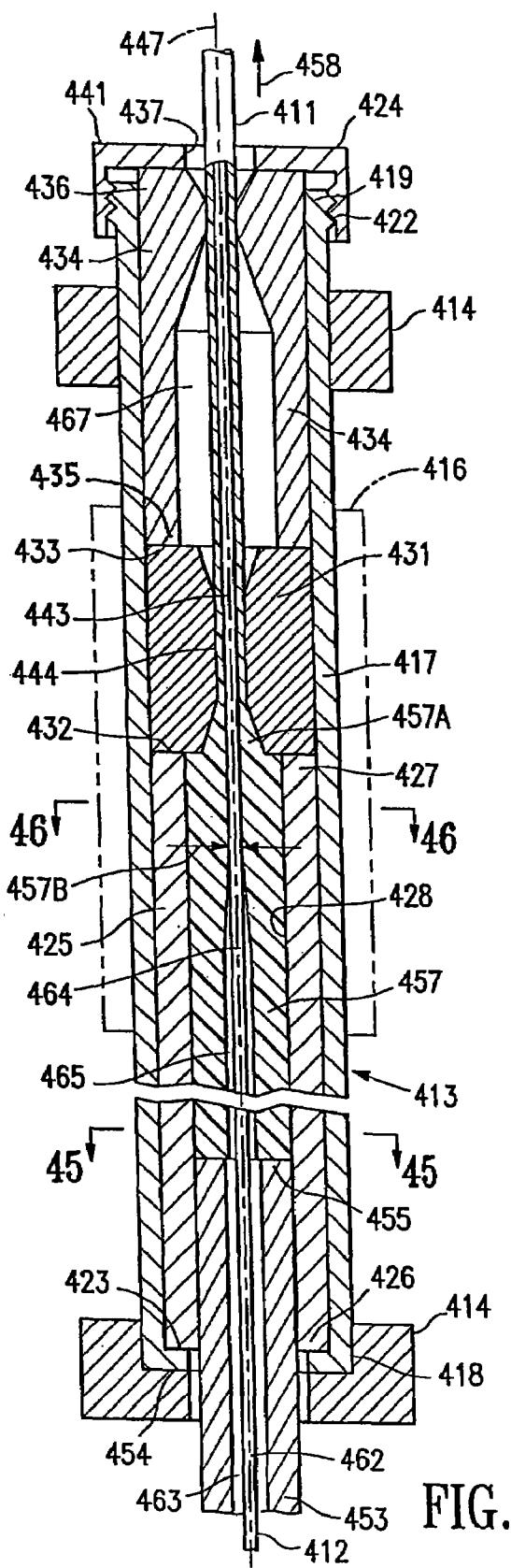
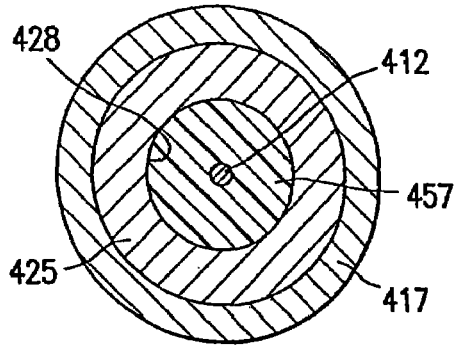
FIG. 46
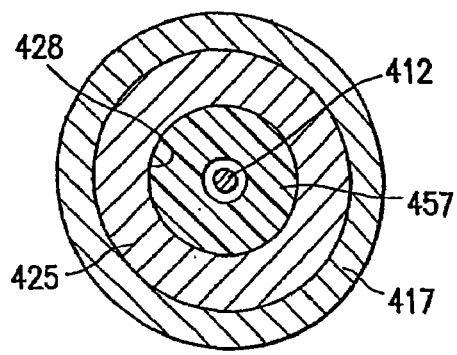
FIG. 45
FIG. 44

POLYMER COATED GUIDE WIRE

CROSS-REFERENCE TO RELATED APPLICATIONS

This is a divisional application of a parent application having U.S. Ser. No. 10/631,275, filed Jul. 31, 2003, which is a divisional application of U.S. Ser. No. 09/441,698, filed Nov. 16, 1999, now U.S. Pat. No. 6,673,025, which is a continuation-in-part application of U.S. Ser. No. 09/203,140, filed Dec. 1, 1998, now U.S. Pat. No. 6,390,993, which is a continuation-in-part application of U.S. Ser. No. 08/868,764, filed Jun. 4, 1997, now abandoned, the contents of all of which are hereby incorporated by reference.

BACKGROUND

This invention relates to the field of guidewires for advancing intraluminal devices such as stent delivery catheters, balloon dilatation catheters, atherectomy catheters and the like within a patient's body, specifically, within a patient's vasculature.

In a typical percutaneous procedure in a patient's coronary system, a guiding catheter having a preformed distal tip is percutaneously introduced into a patient's peripheral artery, e.g. femoral, radial or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the bare wire technique which is used primarily for rail type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed.

The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location if it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guidewire which extends out of the proximal end of the guiding catheter which is outside of the patient. The catheter is advanced over the guidewire, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapable member, which may be the distal extremity of the core member or a separate shaping ribbon which is secured to the distal extremity of the core member, extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.) and U.S. Pat. No. 5,636,641 (Fariabi) which are hereby incorporated herein in their entirety by reference thereto.

Conventional guidewires using tapered distal core sections as discussed above can be difficult to use in many clinical circumstances because they have an abrupt stiffness change along the length of the guidewire, particularly where the tapered portion begins and ends. As a guidewire having a core with an abrupt change in stiffness is moved through tortuous vasculature of a patient, the physician moving the guidewire can feel the abrupt resistance as the stiffness change is deflected by the curvature of the patient's vasculature. The abrupt change in resistance felt by the physician can hinder the physician's ability to safely and controllably advance the guidewire through the vasculature. What has been needed is a guidewire, and particularly a guidewire core member, that does not have an abrupt change in stiffness, particularly in the portions of the distal section that are subject to bending in the vasculature and guiding catheter. What has also been needed is a guidewire with a smooth continuous low friction surface of the guidewire in combination with high strength and flexibility. In addition, it is desirable for a guidewire to have a discrete radiopacity and predetermined size and spacing of radiopaque elements that serve as a measuring guide for determining the size of lesions.

SUMMARY OF THE INVENTION

The guiding member of the present invention has an elongate core member with proximal and distal core sections and a flexible tubular body such as a helical coil or polymeric body disposed about and secured to the distal section of the core member. The distal core section has a plurality of distally tapering contiguous core segments having tapers of up to 25° and lengths of up to 15 cm. As used herein the measurement of tapers is the angle of a line tangent to the surface of the segment in line with the longitudinal axis of the core member. The first tapered core segment, which typically has a circular transverse cross-section, preferably tapers from the diameter of the adjacent proximal core section to a diameter of about half to about three quarters of the diameter of the adjacent proximal core section. The second tapered core segment, which also has a circular transverse cross-section, tapers from the smallest diameter of the first tapered core segment to a diameter of not more than one-half the smallest diameter of the first tapered core segment.

One embodiment includes a first core segment with a taper in the distal direction and a distally contiguous second core segment having a taper in the distal direction greater than the taper of the first core segment. The taper of the first or proximal segment generally can be up to about 5°, preferably about 0.01° to about 1°, more preferably about 0.011° to about 0.2°. The taper of the second or distal core segment can be up to about 6°, preferably about 0.01° to about 1.1°, more preferably about 0.015° to about 0.45°.

In another embodiment, the second tapered core segment has a length greater than the first tapered core segment, with the distal segment generally ranging about 1 to about 12 cm, preferably about 2 to about 10 cm and the distal segment generally about 1 to about 8 cm, preferably about 2 to about 6 cm. The tapered core segments may have circular transverse cross-sections and straight exterior surfaces, e.g. frusto-conical shape. However, other shapes are contemplated, e.g. curved exterior surfaces. Indeed, the taper of the contiguous core segments may have a continuously changing taper over all or part of both core segments.

The flexible tubular body such as a helical coil is secured by its distal end to the distal tip of the distal core section or to the distal tip of a shaping ribbon secured to the distal core section in a conventional fashion. The helical coil may be secured at its distal end by application of an adhesive or epoxy, soldering, brazing or welding to form a rounded distal tip to the guiding member as done with commercially available guidewire for procedures within a patient's coronary artery.

In one embodiment of the invention, the guidewire has an elongate proximal core section having a length of about 65 to about 280 cm and a circular transverse cross-section with a diameter of generally about 0.010 to about 0.035 inch (0.30-0.46 mm), typically about 0.012 to about 0.018 inch (0.30-0.46 mm) for coronary anatomy.

In one embodiment of the invention, the second tapered core segment is preferably followed distally with a manually shapable flattened core segment of about 1 to 4 cm in length which preferably has essentially constant transverse dimensions, e.g. 0.001 by 0.003 inch (0.025 by 0.076 mm). A helical coil having transverse dimensions about the same as the proximal core section is secured by its distal end to the flattened distal tip of the core member, e.g. solder, and by its proximal end at an intermediate position on the second tapered segment so that the distal end of the second tapered segment resides within the interior of the coil. The coil may have a length of about 2 to about 40 cm or more, but typically will have a length of about 2 to about 10 cm in length.

The guidewire of the invention provides the enhanced distal and proximal support needed for stent deployment, advancement of atherectomy devices and the like and provides a smooth transition between the proximal core section and the flattened distal tip of the core member while exhibiting excellent steerability.

In another embodiment, an intracorporeal device, preferably a guidewire, has an elongate member with at least one longitudinal portion having a substantially linear change in stiffness over a length thereof. A substantially linear change in stiffness of a section of an elongate intracorporeal device may be achieved with an elongate core member having a tapered profile, tapering distally to a smaller transverse dimension and configured to produce a linear change in stiffness. The distal taper of the elongate core may be in the form of a taper having a continuously changing taper angle, i.e. a curvilinear taper profile, or may be achieved by a plurality of tapered segments which are longitudinally short in comparison to the longitudinal length of the tapered section as a whole.

In embodiments where a plurality of tapered segments are used, the tapered segments are preferably contiguous or adjacent each other and have a substantially constant taper angle over the length of each tapered segment. In one particular embodiment, the taper angle of each tapered segment is greater than the taper angle of the segment proximally adjacent to it. The taper angle and segment length can be controlled from tapered segment to tapered segment to produce the desired bending characteristics of the longitudinal portion of the core member.

A core member may be ground to a profile which is calculated mathematically to produce a linear change in stiffness. A useful formula for generating a substantially linear change in stiffness is $$D_L = \left[ \frac{64CL}{E\pi} + D_0^4 \right]^{\frac{1}{4}}$$

where $D_L$ is the diameter of an elongate core member at length L from a position of starting diameter $D_0$, E is the modulus of elasticity of the material from which the elongate core member is made, and C is a constant.

This formula may be used to generate smooth continuous profiles, or multiple tapered segments where each individual tapered segment has a substantially constant taper angle. In the latter instance, the taper angle and length of each tapered segment can vary to produce the overall desired effect by having the segmented contour substantially follow the formula above. In one particular embodiment, the points between two adjacent tapered segments, or transition points, have diameters that substantially follow the formula above for $D_L$. As the number of tapered segments increases, this embodiment gradually approaches the smooth continuous curvilinear embodiment. That is, in the limiting case where the number of tapered segments is large, there is little or no difference in stiffness between the segmented core and the smooth curvilinear profile core.

Another approach to generating linear stiffness change in an elongate intracorporeal involves controlling the moment of inertia at any given point in a longitudinal portion. A useful formula for such an approach is $$I_L = \frac{CL}{E} + I_0$$

where $I_L$ is the moment of inertia of the elongate core member at length L from a position of starting inertia $I_0$, E is the modulus of elasticity of the core material, and C is a constant that is derived from the boundary conditions of the longitudinal portion, specifically, a desired starting moment of inertia, finished moment of inertia, length of section of linear change in stiffness.

A core member with a linear change in stiffness over its length provides improved advancement and control of the distal end of an intracorporeal device through a patient's body lumen. The improvement in handling characteristics results in part from the absence of abrupt changes in flexibility that can obscure the tactile feedback to the physician holding the proximal end of the device. In addition, the abrupt changes in stiffness can cause the device to resist smooth and controllable advancement because a step or threshold force must be applied to overcome the abrupt change in stiffness.

Another embodiment of the invention has an elongate core member with a proximal section and a distal section with at least one longitudinal portion having a curvilinear taper. At least one polymer layer is disposed about the distal section of the elongate core member. A flexible body, generally in the form of a helical coil, may be disposed about the distal section of the elongate core member with the polymer layer disposed about the distal section of the elongate core member and dispersed around the helical coil including the cylindrical gap between an inside surface of the helical coil and an outside surface of the elongate core member, if a particular design creates such a gap. The curvilinear taper of the longitudinal portion can be configured to taper distally to a reduced transverse dimension and reduce bending stiffness of the elongate core distally in a smooth and continuous manner. Such a design produces a guidewire having a distal section that can operate within a patient's body and move throughout the patient's body and delivery catheters smoothly without undue sudden resistance felt by the operator as the guidewire is advanced. In one embodiment, the longitudinal portion of the elongate core can be configured to produce a substantially linear change in stiffness along the longitudinal length of the section. In addition, more than one polymer layer can be used. For example, one embodiment has an elongate core member with a proximal section and a distal section, with the distal section having at least one longitudinal portion with a curvilinear taper. A first polymer layer is disposed about the distal section of the core and a second polymer layer is disposed about the first polymer layer.

A desirable feature that can be included with the guidewire embodiments noted above and standard guidewire devices is radiopaque markers disposed at regular or irregular longitudinal intervals in order to facilitate measurement and positioning of intracorporeal structures and devices while performing a procedure. Thus, one embodiment of the invention has an elongate core member with a proximal section and a distal section, a flexible body disposed over the distal section and at least one radiopaque marker disposed on the distal section. The flexible body can consist of a helical coil or a polymer layer, or one or more polymer layers over the helical coil and distal section of the core member. The helical coil can be radiopaque or radiolucent. If the helical coil is radiolucent, the coil may be spaced at desired intervals in order to produce portions of less radiopacity adjacent portions of greater radiopacity. Such a structure creates a pattern that can be seen under flouroscopy and used to measure intracorporeal structure, if the distance between successive radiolucent portions is known. The spaced portions of the radiopaque coil may alternatively be filled with a radiolucent material that can serve to secure the helical coil to the elongate core member. In another alternative, a radiolucent coil could be used as a flexible body with intermittent spaced and stacked portions at known longitudinal intervals. The spaced portions of the coil may then be filled with a radiopaque material which serves to create radiopaque markers at regular intervals, and can also serve to secure the helical coil to the elongate core member at desired locations along the core member.

Another embodiment of the invention can have a flexible body in the form of a tubular polymer member having a plurality of longitudinal segments with at least one of the segments being radiopaque and at least one of the segments being radiolucent. The location, spacing and longitudinal length of the segments can be chosen to create a pattern of radiopaque markers that can be used to measure features under flouroscopic imaging.

In one embodiment, the flexible body member of the guidewire of the present invention is a multi-layered member formed with at least one layer of a polymer material and one layer of radiopaque material. If there are two polymer layers, the radiopaque layer is preferably disposed between the two polymer layers. The radiopaque layer may be continuous or intermittent and comprises elements which have regular or irregular repetitions. The radiopaque layer may also be in the form of an open helical ribbon with one or more adjacent turns of the helical ribbon which do not touch. The helical ribbon is held in place by one or more polymer layers. The radiopaque layer can have sufficient radiopacity to be visualized under a fluoroscope, allowing the physician to use the radiopaque layer not only as a reference tool while advancing the guidewire to a desired intraluminal location, but also as a measuring guide for determining the size of lesions.

The flexible body may be formed about the core member by applying individual layers of polymer to the core member or it may be first formed elsewhere and then secured to the core member by suitable adhesives or by shrink fitting, thus providing a smooth continuous surface. The layer of radiopaque material provides the discrete radiopacity needed for fluoroscopic observation and control of the guidewire.

BRIEF DESCRIPTION OF THE DRAWINGS

FIG. 1 is an elevational view partially in section of a guidewire embodying features of the invention.

FIG. 2 is a transverse cross-sectional view of the guidewire shown in FIG. 1 taken along the lines 2-2.

FIG. 3 is a transverse cross-sectional view of the guidewire shown in FIG. 1 taken along the lines 3-3.

FIG. 4 is an enlarged view of the distal portion of the guidewire shown in FIG. 1 which indicates the tapers of the distal core section.

FIG. 5 is a partial elevational view of the distal core section of an embodiment of the invention which has a separate shaping ribbon extending from the distal extremity of the core member to the distal end of the coil.

FIG. 9 is an elevational view of a portion of a guidewire having features of the invention in partial section.

FIG. 10 is an elevational view in partial section of a portion of a guidewire having features of the invention.

FIG. 17 is an elevational view in partial longitudinal section of a guidewire having features of the invention.

FIG. 18 is a transverse cross sectional view of the guidewire shown in FIG. 17 taken at lines 18-18 of FIG. 17.

FIG. 19 is a transverse cross sectional view of the guidewire shown in FIG. 17 taken at lines 19-19 of FIG. 17.

FIG. 20 is an elevational view in partial longitudinal section of a guidewire having features of the invention.

FIG. 21 is a transverse cross sectional view of the guidewire shown in FIG. 20 taken at lines 21-21 of FIG. 20.

FIG. 22 is a transverse cross sectional view of the guidewire shown in FIG. 20 taken at lines 22-22 of FIG. 20.

FIG. 26 is an elevational view in partial longitudinal section of a guidewire having features of the invention.

FIG. 27 is a transverse cross sectional view of the guidewire shown in FIG. 26 taken at lines 27-27 of FIG. 26.

FIG. 28 is a transverse cross sectional view of the guidewire shown in FIG. 26 taken at lines 28-28 of FIG. 26.

FIG. 29 is an elevational view in partial longitudinal section of a guidewire having features of the invention.

FIG. 30 is a transverse cross sectional view of the guidewire shown in FIG. 29 taken at lines 30-30 of FIG. 29.

FIG. 31 is a transverse cross sectional view of the guidewire shown in FIG. 29 taken at lines 31-31 of FIG. 29.

FIG. 35 is an elevational view in longitudinal section of a tubular polymer member.

FIG. 36 is a transverse cross sectional view of the tubular polymer member of FIG. 35 taken along lines 36-36 in FIG. 35.

FIG. 37 is an elevational view, partially in section, of a guidewire which embodies features of the invention.

FIG. 38 is a transverse cross sectional view of the guidewire of FIG. 37 taken along lines 38-38 in FIG. 37.

FIG. 39 is an elevational view, partially in section, of a guidewire which embodies features of the invention.

FIG. 40A is an alternative embodiment with two layers of a polymer material.

FIG. 40B is an enlarged view of the guidewire shown in FIG. 40A within the circle 40B.

FIG. 41 is an enlarged transverse cross-sectional view of the guidewire shown in FIG. 40B taken along the lines 41-41 in FIG. 40B.

FIG. 42 is an enlarged view of an embodiment of a guidewire in which the radiopaque layer is continuous.

FIG. 44 is an elevational view in partial section of the guide tube assembly shown in FIG. 43 taken along lines 44-44 in FIG. 43.

FIG. 45 is a transverse cross sectional view of the guide tube assembly shown in FIG. 44 taken along lines 45-45 in FIG. 44.

FIG. 46 is a transverse cross sectional view of the guide tube assembly shown in FIG. 44 taken along lines 46-46 in FIG. 44.

DETAILED DESCRIPTION OF THE INVENTION

Figure 6:
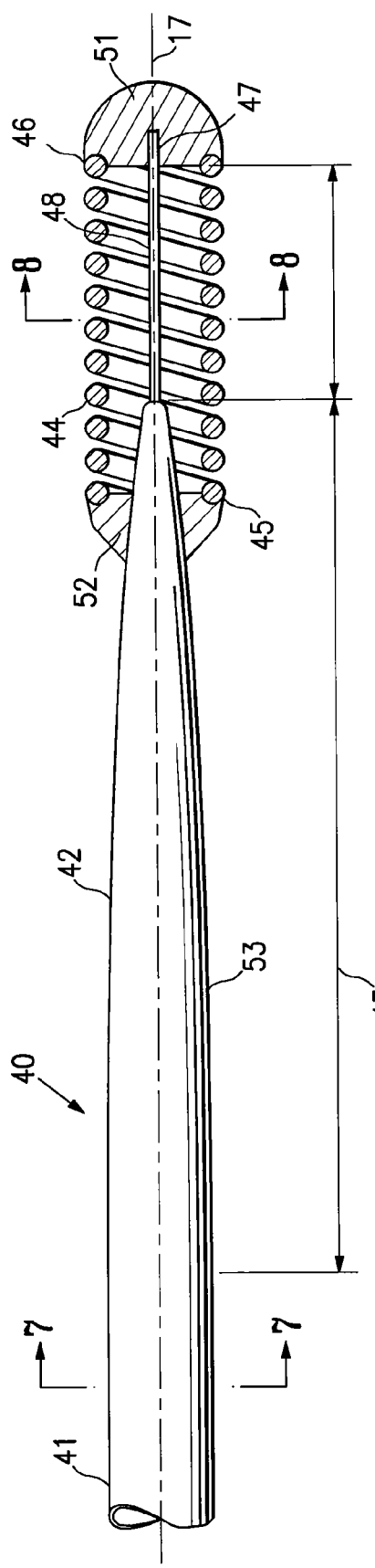
FIG. 6 is an elevational view of a portion of a guidewire having features of the invention.

FIGS. 1-3 depict a guidewire 10 having features of the invention which has a core member 11 with a proximal core section 12, a distal core section 13 and a helical coil 14. The distal core section 13 has a first tapered segment 15 and a second tapered core segment 16 which is distally contiguous to the first tapered core segment. The second tapered segment 16 tapers at a greater degree than the first tapered segment and this additional taper provides a much smoother transition when the distal portion of the guidewire 10 is advanced through a tortuous passageway. The degree of taper of the first tapered core segment 15, i.e. the angle between the longitudinal axis 17 and a line tangent to the first tapered core segment 15 is about 2° to about 10°, whereas the taper of the second tapered core segment 16, i.e. the angle between the longitudinal axis and the second tapered core segment is larger than the first angle and is about 5° to about 10° such as is shown in the enlarged view of the guidewire in FIG. 4. While only two tapered core segments are shown in the drawings, any number of tapered core segments can be employed. Moreover, all of a multiple of tapered core segments need not have increasing degrees of tapers in distal direction. However, two or more contiguous tapered core segments over a length of about 5 to 15 cm should have distally increasing degrees of tapering.

Typically, the first tapered segment is about 3 cm in length and the second tapered segment is about 4 cm in length. In one embodiment, the guidewire 10 has a proximal core section 12 of about 0.014 inch (0.36 mm) in diameter, the first tapered core segment has a diameter ranging from 0.014 inch down to about 0.008 inch (0.36-0.20 mm) and the second tapered core segment has a diameter ranging from about 0.008 to about 0.002 inch (0.20-0.05 mm). A flattened distal tip 18 extends from the distal end of the second tapered core segment 16 to the body of solder 20 which secures the distal tip 18 of the core member 11 to the distal end of the helical coil 14. A body of solder 21 secures the proximal end of the helical coil 14 to an intermediate location on the second tapered segment 16.

The core member 11 is coated with a lubricious coating 19 such as a fluoropolymer, e.g. TEFLON® available from DuPont, which extends the length of the proximal core section 12. The distal section 13 is also provided a lubricious coating, not shown for purposes of clarity, such as a MICROGLIDE™ coating used by the present assignee, Advanced Cardiovascular Systems, Inc. on many of its commercially available guidewires. Hydrophilic coating may also be employed. The proximal section 12, distal section 13, helical coil 14, or any other desired portion of the guidewire 10, or any suitable portion of any other guidewire embodiment described herein, may be coated with either of the two coatings MICROGLIDE™ or TEFLON®, or any other suitable lubricious coating.

The elongate core member 11, and the core member of any other guidewire embodiment discussed herein, may be formed of high strength metals and alloys such as stainless steel, high tensile stainless steel such as hi-ten 304V, precipitation hardenable alloys, including precipitation hardenable stainless steel and other high strength alloys such as MP35N, L605, Elgiloy and the like. The core member 11 may also be made from superelastic, pseudoelastic or shape memory alloys such as NiTi. NiTi alloys or combinations thereof are described in U.S. Pat. No. 5,341,818 (Abrams et al) which is incorporated herein. High strength alloys for use in guidewires are described in U.S. Pat. No. 5,636,641 (Fariabi), which is also incorporated herein by reference.

The helical coil 14 is formed of a suitable radiopaque material such as platinum or alloys thereof or formed of other material such as stainless steel and optionally coated with a radiopaque material such as gold. The wire from which the coil is made generally has a transverse diameter of about 0.003 inch (0.05 mm). The overall length of the coil 14 is typically about 3 cm. Multiple turns of the distal portion of coil 14 may be expanded or stretched to provide additional flexibility.

In the embodiment shown in FIG. 5, the flattened distal segment of the core member shown in FIG. 1 is replaced with a shaping ribbon 3G which is secured at its distal end to the distal end of the coil 14 and at its proximal end to the distal extremity of the core member 11.

While the embodiments described above are directed to tapered segments with constant tapers along their lengths, the taper need not be constant. For example, the tapers of contiguous core segments may be gradually increasing in the distal direction, with the taper, i.e. a tangent line, crossing the junction between the two adjacent tapers being a continuous function. Guidewires are generally about 90 to about 300 cm in length, and most commercially available guidewires for the coronary anatomy are either about 175 cm or about 190 cm in length.

Multiple tapers may be ground simultaneously or as separate operations. A centerless grinder with profile capabilities may be used to grind the tapers simultaneously. A manual centerless grinding may be employed to create separate tapers in separate operations. Tapers may also be formed by other means such as chemical means, e.g. etching, or laser means.

Another embodiment of the invention can be seen in FIG. 6 which is a distal portion of an intracorporeal device in the form of a guidewire 40. The guidewire 40 has an elongate core member 41, with a longitudinal portion 42, the longitudinal portion has a substantially linear change in stiffness along its length 43. The length 43 of the longitudinal portion can be up to 60 cm, specifically about 5 to about 35 cm, more specifically about 10 to about 25 cm. The longitudinal portion 42 tapers distally to a smaller transverse dimension or diameter to a more flexible distal segment. A flexible body 44 having a proximal end 45 and a distal end 46 is secured at its distal end 46 to a distal end 47 of a distal segment 48 of the elongate core member 41 by a first body of solder 51. The proximal end 45 of the flexible body 44 is secured to the longitudinal portion 42 of the elongate core member by a second body of solder 52. The proximal end 45 of the flexible body 44 can be secured to any portion of the elongate core member 41 proximal of the distal end 47 of the distal segment 48.

The longitudinal portion 42, and optionally the entire elongate core member 41 of the guidewire 40, is made from high tensile stainless steel, or hi-ten 304 stainless steel. The longitudinal portion 42 can also be made from other high strength metals or alloys, some of which are precipitation hardenable, such as those discussed above, including 304 stainless steel, MP35N and L605. The longitudinal portion 42 may also be made from pseudoelastic alloys, such as NiTi. The longitudinal portion 42 has a curvilinear profile with a smooth continuous change in taper angle over its length 43. The curvilinear profile of the longitudinal portion 42 can substantially follow the formula $$D_L = \left[\frac{64CL}{E\pi} + D_0^4\right]^{\frac{1}{4}}$$

where $D_L$ is the diameter of the longitudinal portion at length L from a position of starting diameter $D_0$, E is the modulus of elasticity of the core member material, and C is a constant that is determined by the boundary conditions of the longitudinal portion. Such a curvilinear profile generally yields a longitudinal portion 42 having a substantially linear change in stiffness with regard to position along the longitudinal portion.

The constant C is determined by the boundary conditions of a desired section using the equation $$C = \frac{\pi E(D_L^4 - D_0^4)}{64L}$$

where a desired starting diameter $D_0$, finished diameter $D_L$, length of the section having a linear change in stiffness L, and modulus of elasticity E of the section material are inserted into the equation which is then solved for C.

A typical modulus of elasticity for 304 stainless steel is approximately $28 \times 10^6$ psi. An example of a set of values for a longitudinal portion 42 having features of the invention are 0.002 inches for a starting diameter $D_0$, 0.013 inches for a finished or ending diameter $D_L$, 20 cm for the length of the longitudinal portion L, and $28 \times 10^6$ psi for the modulus of elasticity of the core member E. Solving for C yields a constant value of about 0.005 pound-inches. Another example of a set of values for a longitudinal portion 42 having features of the invention are 0.0025 inches for a starting diameter $D_0$, 0.0076 inches for a finished or ending diameter $D_L$, 25 cm for the length of the longitudinal portion L, and $30 \times 10^6$ psi for the modulus of elasticity of the core member E. Solving for C yields a constant value of about 0.00049 pound-inches.

Another approach for achieving a substantially linear change in stiffness in a longitudinal portion 42 of elongate core member 41 is to vary the moment of inertia along the longitudinal portion according to the formula $$I_L = \frac{CL}{E} + I_0$$

where $I_L$ is the moment of inertia of the elongate core member at length L from a position of starting inertia $I_0$, E is the modulus of elasticity of the core material, and C is a constant that is derived from the boundary conditions of the longitudinal portion. The constant C is determined by inserting the values of a desired starting moment of inertia $I_0$, finished moment of inertia $I_L$, length of section of linear change in stiffness L, and modulus of elasticity E into the equation and solving for C.

The moment of inertia of a point on a longitudinal portion 42 or elongate core member 41 can be varied by controlling the diameter in a round cross section as discussed above. Other variations in transverse cross section shape and configuration can be made in embodiments having non-round transverse cross sections. Finally, because bending stiffness is equal to the modulus of elasticity multiplied by the moment of inertia, the bending stiffness may be controlled by adjusting the modulus of elasticity along the length of a longitudinal portion 42 or elongate core member 41 in order to produce a linear change in stiffness along the longitudinal portion.

Figure 8:
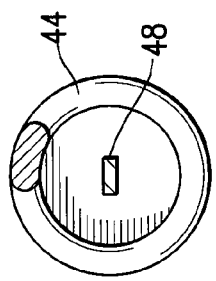
FIG. 8 is a transverse cross sectional view of the guidewire of FIG. 6 taken at lines 8-8 of FIG. 6.
Figure 7:
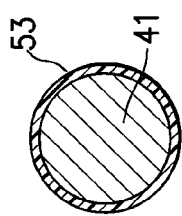
FIG. 7 is a transverse cross sectional view of the guidewire of FIG. 6 taken at lines 7-7 of FIG. 6.

FIG. 7 is a transverse cross sectional view of the guidewire 40 of FIG. 6 taken at lines 7-7 of FIG. 6. The elongate core member 41 is shown having a round cross section. The core member 41 may optionally be coated with a lubricious coating 53. The coating 53 is preferably a hydrophilic polymer, but may also be made of polymers such as TFE or the like. FIG. 8 is a transverse cross sectional view of the guidewire 40 in FIG. 6 taken at lines 8-8 of FIG. 6. The flexible body 44 is in the form of a helical coil which is disposed about the distal segment 48 of the elongate core member 41. The distal segment 48 of the elongate core member is flattened to improve shapability of the distal segment.

FIG. 9 is an elevational view of a guidewire 60 having features of the invention. The guidewire 60 has an elongate core member 61 with a longitudinal portion 62 having a plurality of tapered segments 63 tapering distally to a more flexible distal segment 64. Transition points 65 are disposed between adjacent tapered segments 63. A flexible body member 66 is disposed over the distal segment 64 and the longitudinal portion 62. The flexible body 66 has a proximal end 67 and a distal end 68 with the distal end 68 of the flexible body being secured to a distal end 71 of the distal segment 64 of the elongate core member 61 with a first body of solder 72. The proximal end 67 of the flexible body 66 is secured to the longitudinal portion 62 with a second body of solder 73. The proximal end 67 of the flexible body 66 may also be secured to any suitable portion of the elongate core member 61 or any suitable portion of the distal segment 64. In one embodiment, each tapered segment 63 of the longitudinal portion 62 has a substantially constant taper angle with the taper angle of each tapered segment being greater than the tapered segment proximally adjacent thereto. The diameter of the longitudinal portion 62 at the transition points 65, or alternatively midpoint 74, of the tapered segments can substantially follow the formula $$D_L = \left[ \frac{64CL}{E\pi} + D_0^4 \right]^{\frac{1}{4}}$$

where $D_L$ is the diameter of the longitudinal portion at a transition point at length L from a position of starting diameter $D_0$, E is the modulus of elasticity of the core member material, and C is a constant that is determined by the boundary conditions of the longitudinal portion. The determination of the constant C is performed in a manner similar to the determination of the constant C discussed above with regard to the embodiment of FIG. 6. The tapered segments 63 of the longitudinal portion 62 or core member 61 can be up to 10 inches in length, specifically about 0.1 to about 5 inches in length, more specifically about 0.25 to about 3 inches in length.

FIG. 10 is an elevational view of a guidewire 80 having features of the invention. The guidewire 80 has an elongate core member 81. A shaping ribbon 84 having a proximal end 85 and a distal end 86 has its distal end 86 secured to the distal end 82 of the flexible body 83 with a first body of solder 88. A proximal end 91 of the flexible body 83 and the proximal end 85 of the shaping ribbon 84 are secured to a distal end 89 of a longitudinal portion 92 with a second body of solder 93. The guidewire 80 has a longitudinal portion 92 configured to produce a substantially linear change in bending stiffness similar to the longitudinal portion 42 of FIG. 6.

Figure 11:
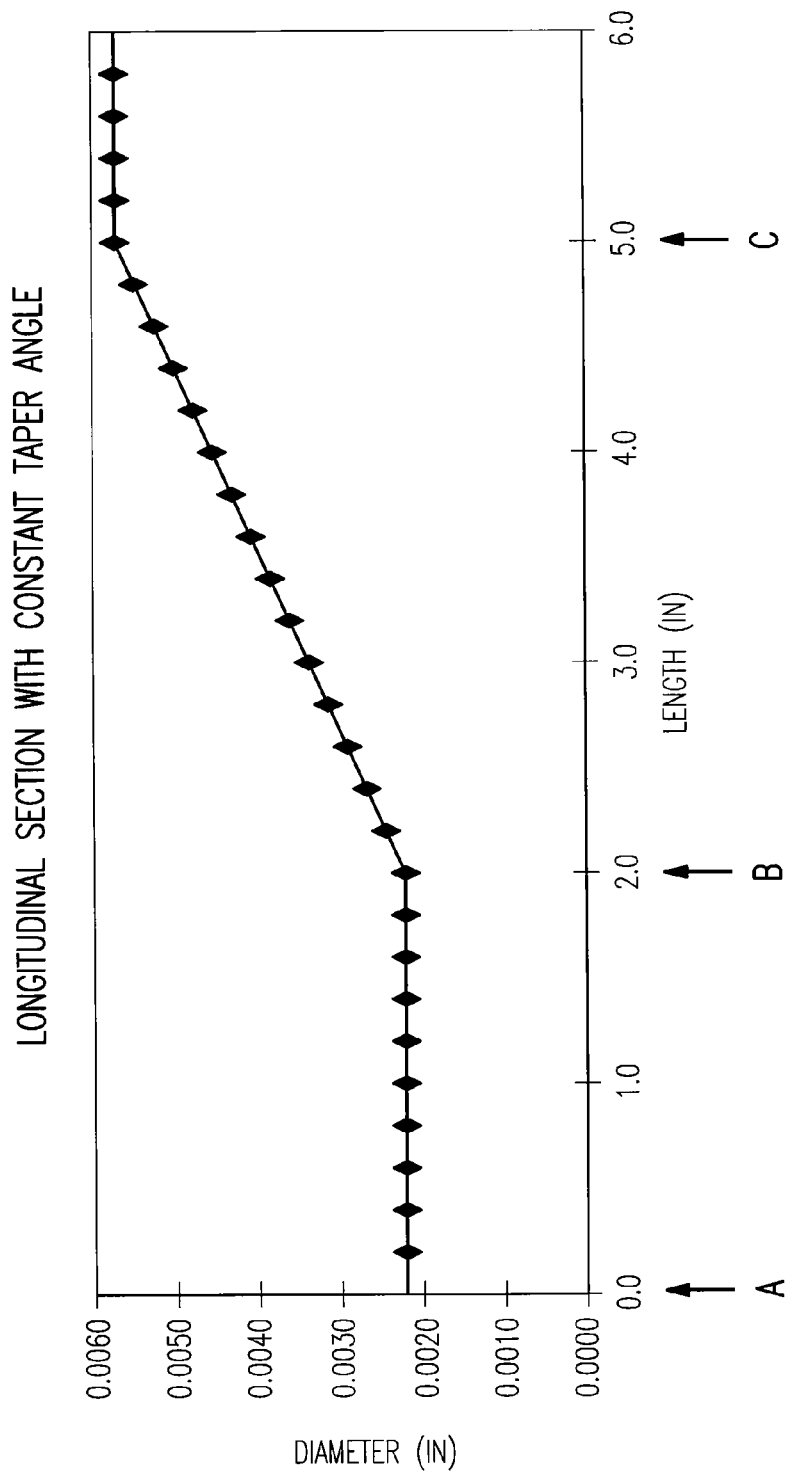
FIG. 11 is a graphic depiction of the diameter of a typical guidewire core member versus the axial position or length from a fixed reference point of that diameter along the core member.

FIG. 11 is a graph of values determined for a typical guidewire core member with diameter being represented in inches along the vertical axis of the graph and length or axial distance from a starting point on the core member represented in inches along the horizontal axis of the graph. At the starting point A of the graph, the diameter of the core member is approximately 0.0022 inches. Point A represents the core at a distal end of a distal segment. The distal segment of the core member continues proximally until the distal end of the tapered longitudinal portion of the elongate core is reached, which is represented by point B on the graph. Moving proximally from the junction of the distal segment and the tapered longitudinal portion, the diameter of the core member increases proportionally with a length from the junction. This type of tapered longitudinal portion is representative of a typical tapered guidewire section having a constant taper angle over the length of the section. The taper diameter increases proximally until the junction between the tapered longitudinal portion meets the constant diameter section of the elongate core which is represented by point C on the graph.

Figure 12:
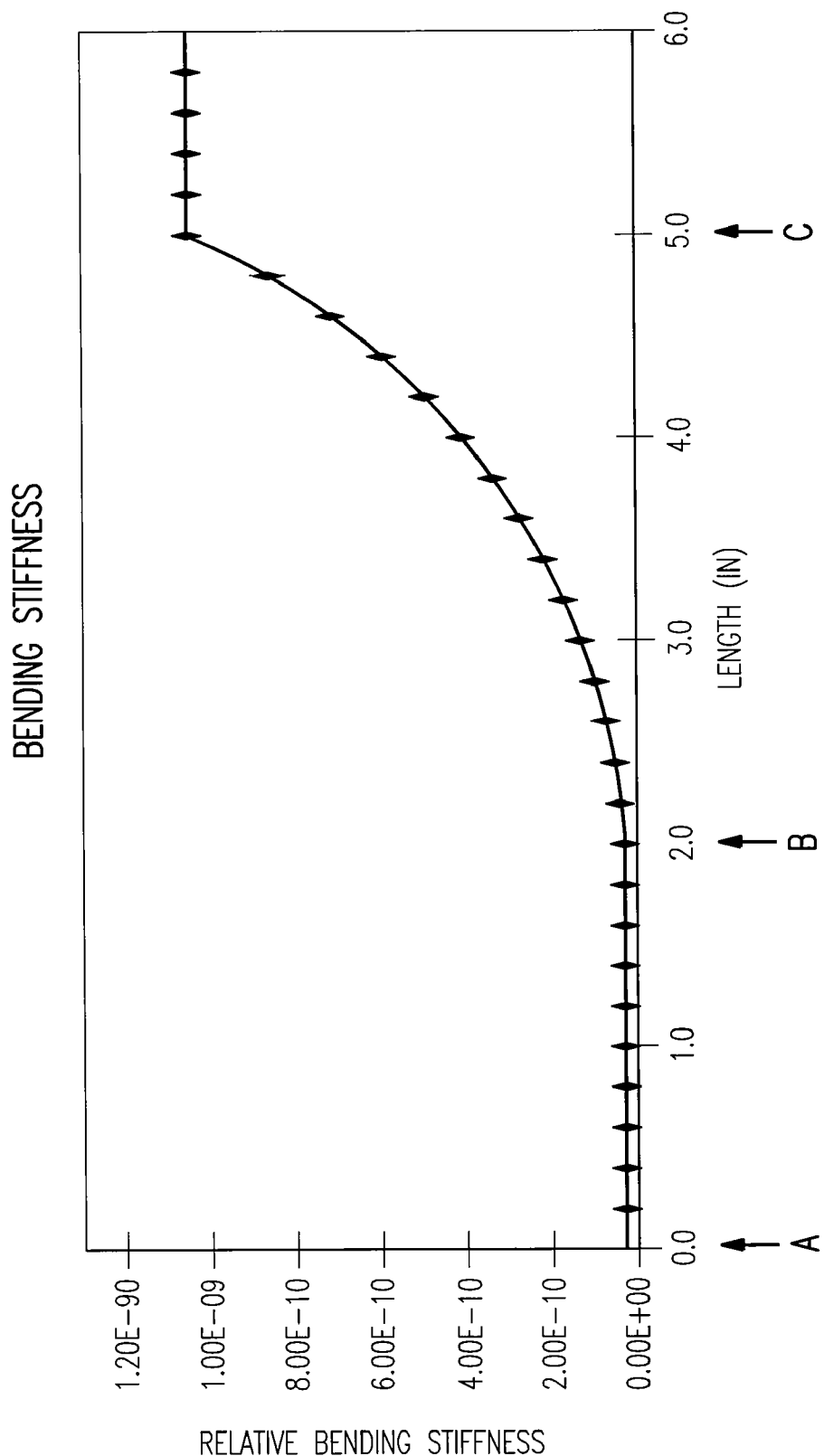
FIG. 12 is a graphic depiction of relative bending stiffness values of a typical guidewire core member versus length from a reference point along the core member.

FIG. 12 is a graph of relative bending stiffness values of the elongate core member of FIG. 11 along its axial length. As can be seen from the graph of FIG. 12, the plot of bending stiffness of the tapered longitudinal portion starting at point B and proceeding proximally to point C is not a straight line. There is a curvature to the plot which becomes progressively steeper as point C is approached. Near point C, the plot becomes quite steep, which represents an abrupt change in bending stiffness in the vicinity of point C.

Figure 13:
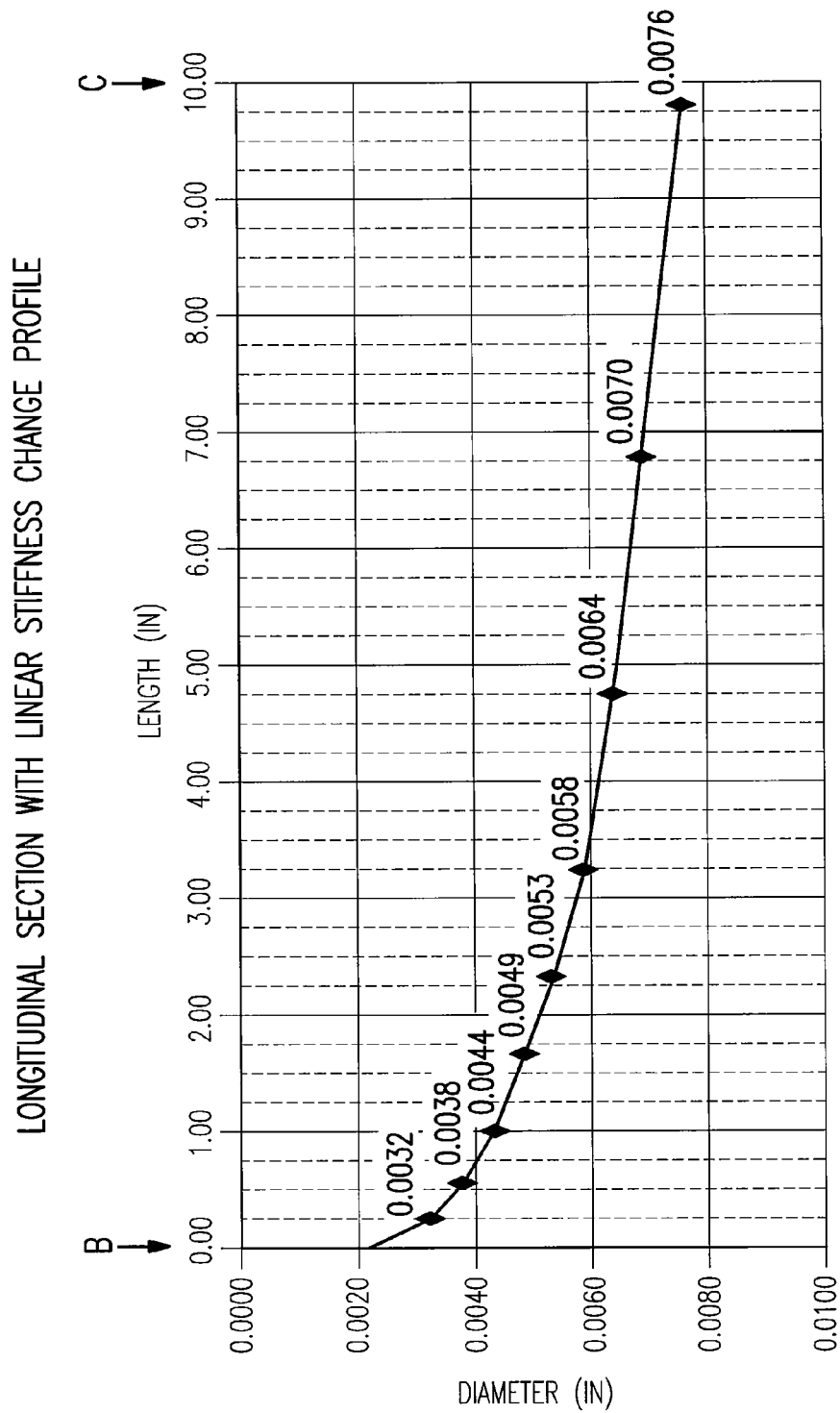
FIG. 13 is a graphic depiction of the diameter of a typical guidewire core member versus the length from a fixed reference point or longitudinal position of that diameter.

FIG. 13 is a plot or graph of the diameter of a guidewire core versus the axial position of the diameter in a core having a longitudinal portion with a substantially linear change in bending stiffness. The graph begins at point B at length 0 with the core member having a diameter of about 0.002 inches. Point B of FIG. 13 has a similar starting diameter to point B in FIG. 11. FIG. 13 is representative a graph of stiffness values for an embodiment of the invention having a plurality of tapered segments, with each tapered segment having a substantially constant taper angle. The change in diameter or taper angle of the tapered segments is greater at the distal end of the longitudinal portion and decreases proximally. The slope of the graph or taper angle for each tapered segment is less than that of the tapered segment that is distally adjacent. The profile of transition points between each pair of adjacent tapered segments of the longitudinal portion depicted by the graph of FIG. 13 substantially follows the formula $$D_L = \left[\frac{64CL}{E\pi} + D_0^4\right]^{\frac{1}{4}}$$

where $D_L$ is the diameter of the longitudinal portion at a transition point at length L from a position of starting diameter $D_0$, E is the modulus of elasticity of the core member material, and C is a constant that is determined by the boundary conditions of the longitudinal portion.

Figure 14:
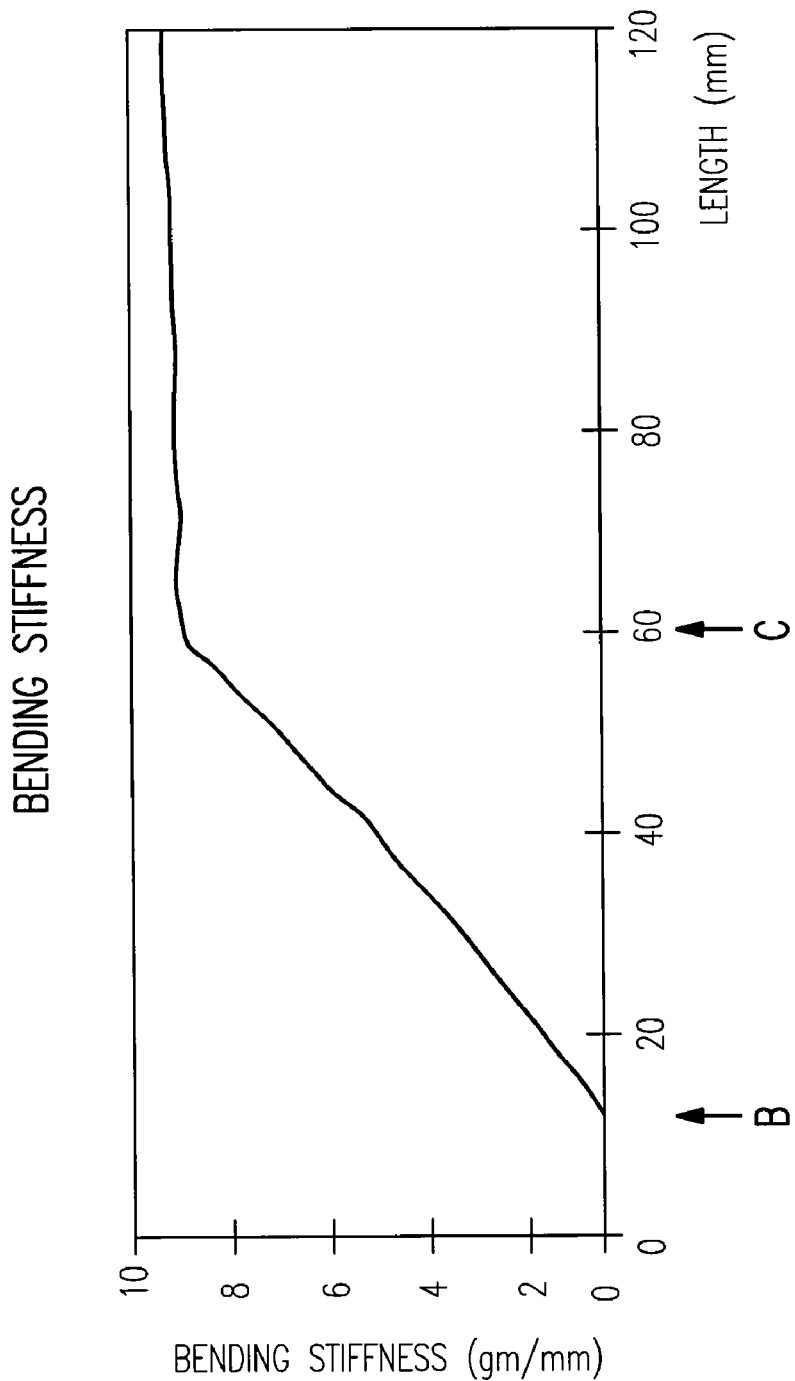
FIG. 14 is a graphic depiction of relative stiffness values of a typical guidewire core member versus longitudinal position or length along the core member.

FIG. 14 depicts typical relative bending stiffness values of a core member versus axial or longitudinal position along the length of the core member. The core member has a longitudinal portion with a taper profile configured to generate a linear change in bending stiffness. The plot from point B to point C does not change appreciably in slope which indicates a constant change in stiffness over that section. This graph is not indicative of the progressively steeper slope found on the stiffness curve of FIG. 12 where an abrupt change in stiffness is noted at point C, in addition to other points.

Bending stiffness can be measured in a variety of ways. Typical methods of measuring bending stiffness include extending a portion of the sample to be tested from a fixed block with the sample immovably secured to the fixed block and measuring the amount of force necessary to deflect the free end of the sample, i.e., the end that is away from the fixed block, a predetermined distance. A similar approach can be used by fixing two points along the length of a sample and measuring the force required to deflect the middle of the sample by a predetermined amount of displacement. Those of ordinary skill in the art will realize that a large number of variations on these basic methods exist including measuring the amount of deflection that results from a fixed amount of force on the free end of a sample, and the like. Although the graph of FIG. 14 shows relative bending stiffness in terms of grams per millimeter, the values shown were derived from a specific test apparatus using the methods discussed above. Other methods of measuring bending stiffness may produce values in different units of different overall magnitude.

Figure 15:
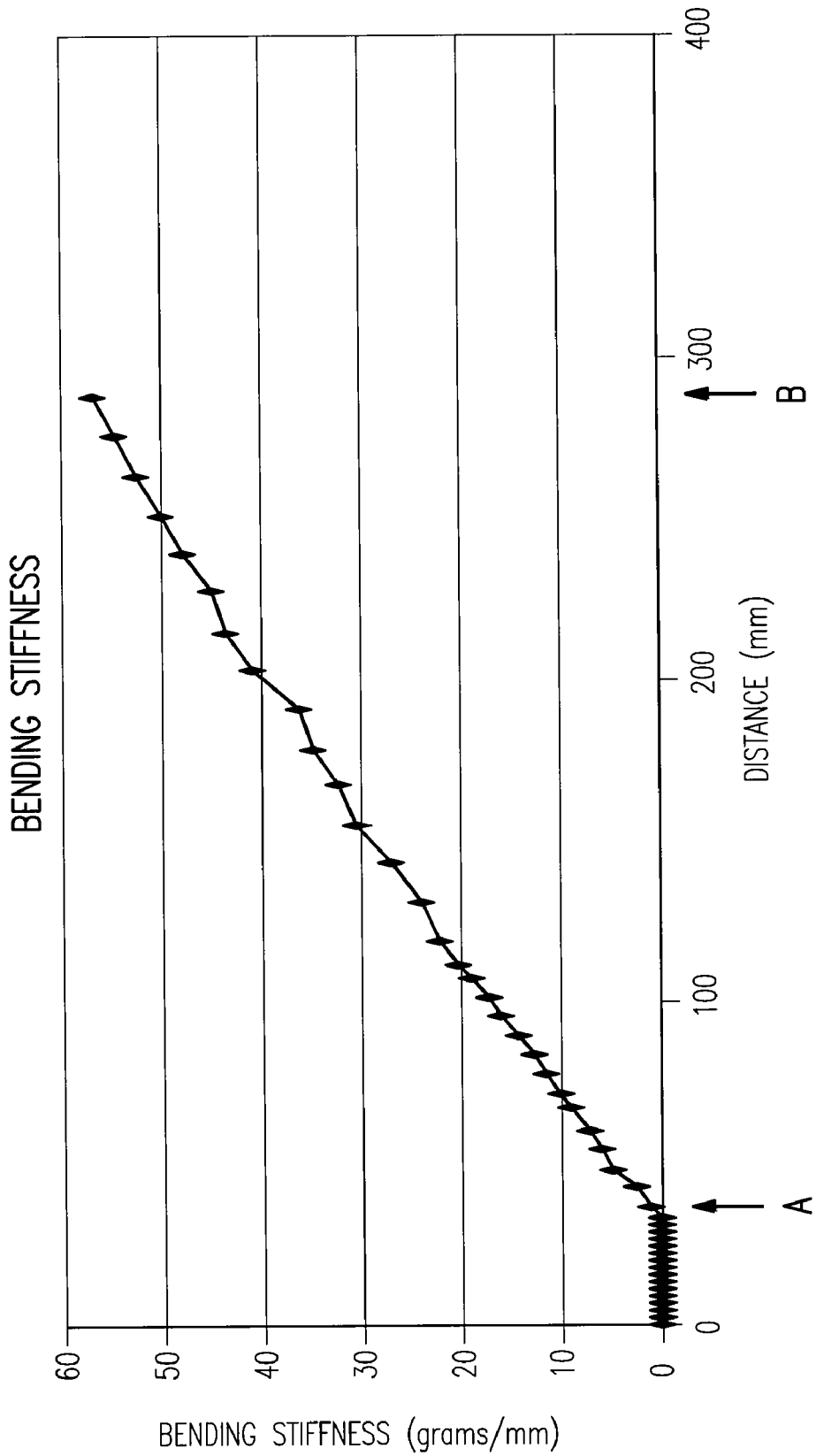
FIG. 15 is a graphic depiction of relative stiffness values of a typical guidewire core member versus longitudinal position or length along the core member.

FIG. 15 depicts typical relative bending stiffness values of a longitudinal portion of another embodiment of a core member versus axial position along the core member. The slope of the graph from point A to point B is essentially constant, indicating a substantially constant change in bending stiffness from point A to point B.

Figure 16:
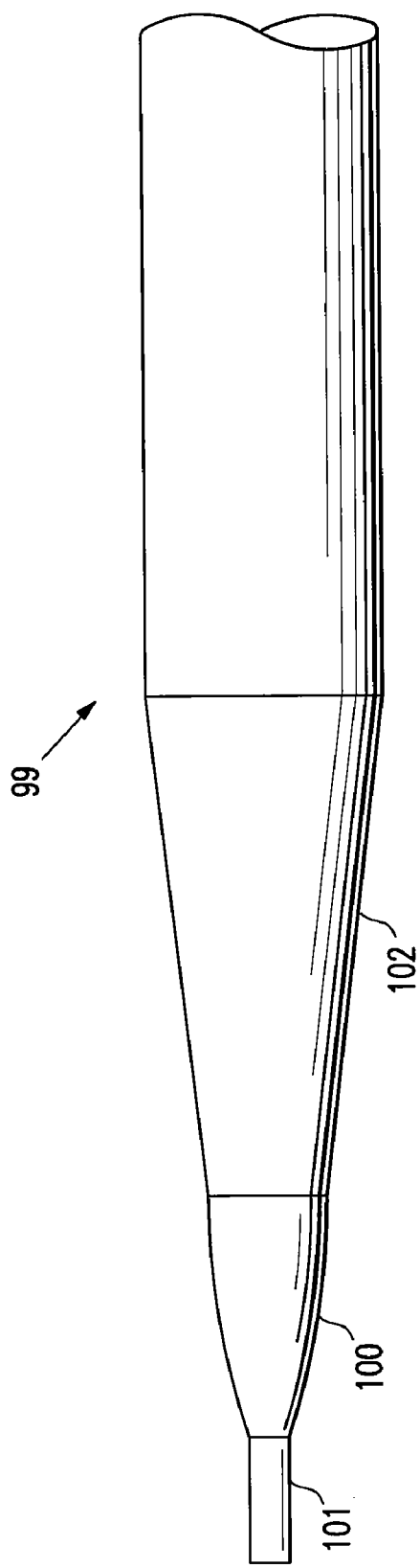
FIG. 16 is an elevational view of a section of a guidewire having features of the invention.

It may be desirable to have multiple tapered longitudinal portions or sections having a varied flexibility. Any combination of multiple longitudinal portions may be used including sections having a substantially constant taper angle, sections having a substantially linear change in stiffness along a length thereof, or sections of substantially constant diameter along a length thereof. In FIG. 16, an embodiment of an elongate core member 99 has a longitudinal portion 100 of substantially linear change in stiffness intermediate to a distal segment 101 having a substantially constant diameter and a constant taper section 102 with a constant taper angle increasing in diameter proximally. The distal segment 101 has a diameter of about 0.002 to about 0.003 inches, and a length of about 3 to about 6 cm. The longitudinal portion 100 having a substantially linear change in stiffness is about 15 to about 25 cm in length and tapers to an increased diameter proximally from about 0.002 to about 0.003 inches at a distal end of the longitudinal portion to about 0.0065 to about 0.0085 inches at a proximal end of the longitudinal portion. The constant taper section 102 tapers proximally from a diameter of about 0.0065 to about 0.0085 inches at its distal end to an increased diameter of about 0.012 to about 0.014 inches at its proximal end.

FIGS. 17-19 show a guidewire 110 having an elongate core member 111 with a proximal section 112 and a distal section 113. The distal section 113 has a longitudinal portion 114 with a curvilinear taper 115 tapering distally to a reduced transverse dimension. A distal segment 116 is disposed at a distal end 117 of the longitudinal portion 114 which is flattened to form a more shapable distal end of the guidewire. An optional flexible body 121 in the form of a proximal helical coil 122 and a distal helical coil 123 is disposed about the distal section 113 of the elongate core member 111 and the distal segment 116. The proximal helical coil 122 is secured at its distal end 122A to a proximal end 123A of the distal coil 123 by a body of solder 121A. A proximal end 122B of the proximal helical coil 122 is secured to the elongate core member 111 on the longitudinal portion 114 with a body of solder 122C. A distal end 123B of the distal helical coil 123 is secured to the distal end 124 of the distal segment 116 by a body of solder 125. The body of solder 125 can provide an enlarged body relative to a transverse dimension of the distal segment 116 which serves to mechanically secure the polymer layer 126 and helical coil 121 to the distal segment. A polymer layer 126 is disposed about the distal section 113 of the elongate core member 111 and the helical coil 121. A lubricious coating 127 is optionally disposed on an outer surface 128 of the elongate core member 111 and an outer surface 131 of the polymer layer 126. A hydrophilic polymer coating may be used for lubricious coating 127 or any other lubricious coating discussed herein with regard to other embodiments. Other lubricious materials such as HYDROGLIDE™ and TEFLON® may also be used on any of the embodiments discussed herein.

In one embodiment, the lubricious coating 127 generally includes a base coat and a top coat. The base coat has a binding component and a grafting component, and is used to strongly adhere to the surface of the device and also to strongly bond to the top coat. Specifically, the binding component binds to both the top coat and to the grafting component, and the grafting component adheres to the device surface. The base coat containing the grafting component and binding component in a suitable carrier such as a solution is first applied to the surface of the device. The base coat is preferably polymerized, e.g., exposed to polymerizing radiation to polymerize the grafting component, and the grafting component is bonded to the binding component and adhered to the surface of the device to form a base coat on the device. The device is then coated with a top coat containing a desired therapeutic, diagnostic, or hydrophilic agent.

The top coat may be applied in a solution which is allowed to evaporate, to form a top coat with a therapeutic, diagnostic, or hydrophilic agent. In another embodiment, the device is coated with a top coat comprising a linking agent, and the linking agent is exposed to the therapeutic, diagnostic, or hydrophilic agent to form a complex therewith, to thereby form the therapeutic, diagnostic or hydrophilic coating of the invention. Because the top coat bonds to the base coat, the therapeutic, diagnostic, or hydrophilic coating produced will not readily wear off.

In one embodiment, the base coat comprises a binding component which is a homofunctional compound having homofunctional groups which covalently bond to functional groups in the top coat. In a preferred embodiment, the homofunctional binding component is grafted to the grafting component by a hydrogen abstraction mechanism, in which the grafting component is activated by initiators and covalently bonds to the binding component. In another embodiment, the base coat comprises a binding component which is a heterofunctional compound having a first functional group for covalently bonding with the grafting component, and a second functional group for covalently bonding to functional groups in the top coat.

As mentioned above, the binding component of the base coat bonds to the top coat. In one embodiment, the therapeutic, diagnostic, hydrophilic or other active agent has functional groups which directly bond to functional groups of the binding component. In another embodiment, the therapeutic, diagnostic, or hydrophilic agent is bound to the binding component by a linking agent in the top coat. The linking agent may inherently have functional groups, or may be modified to include functional groups, which bond to functional groups of the binding component. The linking agent may be bound to the base coat and thereafter exposed to the therapeutic, diagnostic or hydrophilic agent, or alternatively, the linking agent may be exposed to the agent before or during the binding of the linking agent to the base coat.

A variety of suitable linking agents may be used, including avidin-biotin complexes, and functionalized liposomes and microsponges and microspheres. Avidin is a polypeptide composed of at least 128 amino acid residues. Typically however, the single polypeptide chain is a subunit associated with three essentially identical polypeptide chains, forming a tetramer. Avidin as a receptor is typically used in conjunction with its highly specific ligand, biotin, $C_{10}H_{16}N_2O_3S$. An avidin tetramer will bind 4 biotin molecules in solution in a noncovalent interaction which has a binding constant of about $10^{15}$ $M^{-1}$, a half-life in vivo of about 89 days, and which is essentially undisturbed by organic solvents.

Biotinylation, or the process of covalently binding biotin to another molecule, typically takes place by N-hydroxysuccinimide binding. Spacer molecules may be inserted between the avidin and the base coat, or between the biotin and the therapeutic or diagnostic agent, as is known in the art, to facilitate avidin-biotin binding or improve the activity of the therapeutic or diagnostic agent. The avidin or the biotin molecule may be chemically altered to decrease the binding constant, to thereby tailor the dissociation rate in vivo, and provide controlled release of the therapeutic or diagnostic agent bound thereto. Avidin and biotin are available from a variety of commercial suppliers, such as Sigma.

In one embodiment, avidin covalently binds to the binding component of the base coat, and binds to a biotinylated therapeutic or diagnostic agent, such as a biotinylated protein, antibody, peptide or oligonucleotide. However, the avidin-biotin linking agent may alternatively have biotin moieties covalently bound to the binding component of the base coat, and avidin moieties bound to the therapeutic or diagnostic agent. Alternatively, biotin may be covalently bound to the base coat and to the therapeutic or diagnostic agent, with avidin, by virtue of its multivalency with biotin, binding the two biotin moieties together.

In another embodiment, a base coat is not used, and a lubricious coating 127 is provided, which is a hydrophilic coating generally including a hydrophilic polymer, an ionic compound with at least one inorganic ion, and a grafting component. The grafting component is polymerized as outlined above, so that the grafting component grafts to the device and crosslinks to the hydrophilic polymer, to form a hydrophilic coating on the device. When the coated device is hydrated, the coating absorbs water and is highly lubricious, but does not dissolve in the aqueous or blood medium because the hydrophilic polymer is immobilized by the grafted network. Moreover, the ionic compound, or salt, increases the lubricity of the hydrophilic coating by providing uncrosslinked domains in the crosslinked matrix.

Because the ability of a hydrophilic polymer to absorb water is decreased when the polymer is crosslinked, the salt enhances the polymer lubricity by disrupting the crosslinking of the hydrophilic polymer into the grafting component crosslinked network. Therefore, when the hydrophilic coating is hydrated by exposure to a solvent and the salt dissolves, these uncrosslinked domains provide additional lubricity by increasing the contact between the hydrophilic polymer and the countersurface, e.g. the patient's vessel wall, and hence additional lubricity.

The coating can be applied to any device having a polymeric surface, as for example, a catheter formed of conventional materials, or a metal device, such as a metal guidewire or stent, having a polymer primer coat. For example, the catheter components may be formed of high density polyethylene, polyethylene terephthalate, and polyolephinic ionomers such as Surlyn®, nylon and the like which are frequently used to form dilatation balloons or catheter shafts. Additionally, the therapeutic, diagnostic, or hydrophilic coating of the invention can be applied directly to a metal device. For example, in the embodiment of the invention having a base coat and a top coat, the base coat adheres, as by Van der Waals forces, to the metal surface of the device, so that a polymeric primer coat need not be used.

In the embodiment of the coating of the invention having a hydrophilic agent, the coated device has a superior hydrophilic coating which is highly lubricious against biological tissue and is strongly bound to the device surface due to the grafting component used alone or in combination with the binding component. In the case of a guidewire, the coating serves to enhance device access to distal lesions and the ease with which a device crosses small diameter athlerosclerotic lesions.

The elongate core member 111 can be made from a high tensile strength stainless steel, preferably Hi-Ten 304V stainless steel. The elongate core member 111, and the elongate core member of other guidewire embodiments discussed herein, can also be made from a variety of other suitable materials including superelastic and pseudoelastic alloys such as NiTi, stainless steels such as 304V and 316L, precipitation hardenable alloys such as precipitation hardenable stainless steel, MP35N, L605, Elgiloy and the like. The transverse dimension of the proximal section 112 of the elongate core member can be from about 0.005 to about 0.040 inches, specifically about 0.01 to about 0.018 inches, and more specifically about 0.013 to about 0.015 inches.

The transverse cross section of the proximal section 112 of the elongate core member is shown as circular, but can also have any other suitable cross sectional configuration such as elliptical, triangular, square or rectangular. The transverse dimension of the proximal section 112 of the elongate core member is typically constant over at least a substantial portion of its length, however, the proximal section may also have tapered longitudinal portions.

The distal section 113 of the elongate core member 111 has a longitudinal portion 114 and a distally contiguous distal segment 116. The distal segment 116 may be a continuation of the elongate core member 111 as shown, or it may be a separate shaping ribbon secured to the elongate core member by adhesives, epoxies, soldering, welding or the like. The longitudinal portion 114 has a curvilinear taper 115 tapering in a distal direction to a smaller transverse dimension. As discussed above, the proximal section of the elongate core member may have a transverse dimension of about 0.005 to about 0.04 inches, specifically about 0.01 to about 0.018 inches, and more specifically about 0.013 to about 0.015 inches. The longitudinal portion 114 tapers from the nominal transverse dimension of about 0.014 inches at a proximal end of the longitudinal portion to a transverse dimension of about 0.005 inches at the transition between a distal end of the longitudinal portion 114 and a proximal end of the distal segment 116.

The curvilinear taper 115 of the longitudinal portion 114 may be of any suitable profile which produces a smooth transition in flexibility, without abrupt changes in transverse cross section resulting in abrupt changes in flexibility which can adversely affect a user's tactile feel during advancement of the guidewire into an itracorporeal space. The profile of the curvilinear taper 115 may yield a linear change in stiffness with regard to axial position as discussed above.

Generally, the length of the longitudinal portion 114, and other longitudinal portions of guidewire embodiments discussed herein, may be of a significant value relative to the overall length of the elongate core 111. More specifically, the length of the longitudinal portion should be at least 2 or 3 times the transverse dimension of the elongate core at the location of the section. The longitudinal portions of the invention discussed herein are not generally meant to encompass the short transitions between tapered sections of constant taper angle of guidewire cores known in the art. Short transition portions of guidewire cores between tapered sections of constant taper angle may have a variety of profiles, including curvilinear, due to imperfections in the tools used to cut or grind the cores. A longitudinal portion of the present invention can be of a length sufficient to produce a measurable effect on guidewire performance, as mentioned above, at least 2 to 3 times the transverse dimension of the elongate core. Typically, the longitudinal portion 114 can have a length of about 0.1 to about 60 cm, specifically about 5 to about 35 cm, more specifically about 15 to about 25 cm.

The distal segment 116 is configured to produce shapability and can have a length of about 0.5 to about 15 cm, specifically about 2 to about 10 cm, and more specifically about 4 to about 6 cm. The distal segment 116, and the distal segment of other embodiments of the invention discussed herein, may have a variety of configurations to facilitate shapability and prevent prolapse during use. Some of the configurations include a stepped taper, tapered flat, compound taper and the like. Stepped tapered configurations of the distal segment can include a single step flat, or multiple step flats, with 2 to 10 steps being preferred, and 3 to 5 steps being typical.

In one embodiment, the distal segment 116 can have at least two opposed tapered faces tapering distally over the length of the distal segment to a smaller transverse separation. Optionally, the opposed tapered faces of a distal segment may be mirror images of each other and parallel to each other as well as distally tapering at the edges. Also, the tapered faces may have a curved profile in a longitudinal direction or they may have a straight surface profile in a longitudinal direction.

The distal helical coil 123 can be formed, at least in part, of a radiopaque metal such as a platinum-nickel or platinum-iridium-tantalum alloy. The proximal helical coil 122 can be made from 304V stainless steel. Other materials suitable for the proximal helical coil 122 and the distal helical coil 123, and suitable for the helical coils of other embodiments of the invention discussed herein, can include radiopaque metals and alloys such as gold, platinum, platinum iridium, tungsten, tantalum and radiolucent metals such as 304 and 316 stainless steel, MP35N, L605 and Elgiloy, and any combination thereof. The use of multiple coil segments as well as a method of joining various coil segments for use in guidewires can be found in U.S. Pat. No. 4,538,622 (Samson et al.), which is hereby incorporated by reference herein in its entirety.

Generally, the flexible body 121 has an inner transverse dimension suited for positioning of the flexible body 121 over the distal segment 116 and the distal section 113 of the elongate core member 111, including a portion of the longitudinal portion 114. As noted above, the helical coils 122 and 123 can be secured to the elongate core member 111 and distal segment 116 by soldering. However, the helical coils 122 and 123 may also be secured to each other, the elongate core member 111, or the distal segment 116 by an epoxy, adhesive, weld or the like. Alternatively, the helical coils 122 and 123 may be held in place by the polymer layer 126 which covers the flexible body 121 and the distal section 113 of the elongate core member 111.

The helical coils 122 and 123 can be made from round wire stock or from material having alternative cross sectional shapes such as flat ribbon and semicircular. The wire stock of helical coils 122 and 123 can have a transverse dimension of about 0.0005 to about 0.01 inches, specifically about 0.001 to about 0.005 inches, and more specifically about 0.002 to about 0.004 inches. The helical coils 122 and 123 can have adjacent coil spacing of up to about 200%, specifically about 20% to about 100%, and more specifically about 55% to about 65%. Coil spacing percentage as used herein is defined as the percentage of the distance between adjacent coil loops relative to the thickness or transverse dimension of the coil material or stock. For example, a coil wound from round wire stock having a diameter of 0.003 inches with a gap or space between adjacent coil loops of 0.003 inches would have 100% coil spacing.

The alternative to a spaced helical coil is a stacked helical coil with each individual loop of the coil in contact with adjacent coils or coil loops, corresponding to a zero coil spacing percentage. In addition, the helical coils 122 and 123 may be partially spaced and partially stacked or have varying percentage spacing over its length, or any combination of these variations. Any of the properties of helical coils 122 and 123 described above can be shared with the helical coil of other embodiments of the invention described herein.

The polymer layer 126 may completely or partially encapsulate the distal section of the elongate core member 111. The polymer layer generally makes contact with the distal section 113, of the elongate core member 111 where there is no flexible body 121. In areas of the elongate core member 111 covered by helical coils 122 or 123, the polymer layer 126 may be applied over the helical coils and not penetrate into the coils, or the polymer layer 126 may be applied so as to penetrate helical coils 122 and 123 and make contact with the elongate core member 111, thereby completely encapsulating the helical coils and elongate core member where the polymer layer is so applied.

The polymer layer 126 may also be configured to penetrate the helical coils 122 and 123, or any similar flexible body 121, to any desired intermediate degree. For example, the polymer layer 126 could be configured to penetrate helical coils 122 and 123 completely, but not make contact with the elongate core member 111 or distal segment 116. The body of solder 125 may optionally be left uncoated by the polymer layer 126 in order to partially expose the body of solder 125.

The polymer layer 126 has an outer transverse dimension similar to that of the proximal section 112 of the elongate core member 111 which provides a guidewire with a substantially constant outer transverse dimension which translates smoothly in an axial direction within catheter lumens, intracorporeal channels, or the like. The outer transverse dimension of the polymer layer 126 can also be varied along the axial length thereof in order to produce a tapered outside dimension over the effected area of the guidewire 110. Such a tapered outside dimension can be configured to taper distally or proximally to a reduced transverse dimension.

The polymer layer 126, and any of the polymer layers discussed herein, can be made from a variety of suitable polymers, including polyurethanes, including polyurethane thermoplastic elastomers; polyamides (nylons); polyethers; polyesters; polyacetals; acrylics; methacrylics; cellulosics; fluoropolastics; epoxies; keton-based resins and polymers; polyimide based resins and polymers; bismaleimides; nitrites; polyarylates; polycarbonates; liquid crystal polymers; terephthalate resins and polymers including polybutylene terephthalate and polyethylene terephthalate; polyetherimides; polyolefins including polyethylenes, polypropylenes, polybutylenes, polybutadienes; polyvinyls including polystyrenes and polyvinyl chlorides; elastomers especially thermoplastic elastomers; silicones; rubbers; ionomers; ceramers; dendritic polymers; and derivatives, copolymers, multipolymers, blends and/or mixtures of any of the previous listed resins and polymers within each group and between each group. This latter includes polyether block amide elastomers such as COPA and PEBAX.

Any of the aforementioned polymers may be loaded with additives to control the physical properties such as flexural modulus, hardness, and radiopacity. The shore hardness of the polymer layer 126 can range from about 50A to about 55D, preferably about 80A to about 50D, and more preferably about 85A to about 95A.

The axial length of the polymer layer 126 can be configured to cover the entire length of the guidewire, but generally has a length coextensive with the distal section 113. The axial length of the polymer coating is typically from about 5 cm to about 50 cm, preferably about 10 to about 45 cm, and more preferably about 30 to about 40 cm. The polymer layer 126, and any of the other polymer layers discussed herein, can be applied by heat shrinking, dipping, spraying, painting, vapor deposition, coextrusion, molding or the like. The polymer layer 126 can be polyurethane applied by an extrusion process which produces a polymer layer having a substantially constant outer diameter and produces a smooth continuous outer surface. Such a process is described subsequently herein.

FIGS. 20-22 show a guidewire 140 having an elongate core member 141 with a proximal section 142 and a distal section 143. The distal section 143 has a longitudinal portion 144 with a curvilinear taper 145 tapering distally to a reduced transverse dimension. A distal segment 146 is disposed at a distal end 147 of the longitudinal portion 144 which is flattened to form a more shapable distal end of the guidewire 140. An optional flexible body in the form of a helical coil 151 is disposed about the distal section 143 of the elongate core member 141. The helical coil 151 has a proximal end 152 and a distal end 153. A first polymer layer 156 is disposed about the distal section 143 of the elongate core member 141 and the helical coil 151. A second polymer layer 157 is disposed about an outer surface 161 of the first polymer layer 156.

A lubricious coating 162 is optionally disposed on an outer surface 163 of the elongate core member 141 and an outer surface 164 of the second polymer layer. In some embodiments, the materials and dimensions of the first polymer layer 156 and second polymer layer 157 can be chosen to have differing properties to facilitate manufacture of the guidewire 140 and enhance the performance of the guidewire. In one embodiment, the first polymer layer 156 can be made of an ultraviolet light curable material, specifically, a U.V. curable polyurethane, that can be applied by dipping or spraying over the distal section 143 of the guidewire and then cured by exposing the material to ultraviolet radiation. Applying and curing a thin U.V. adhesive or the like over the distal section 143 and helical coil 151 reduces movement of the helical coil 151 in relation to the distal section 143 which makes the subassembly more stable as the second polymer layer 157 is applied. In addition, a thin layer of U.V. curable polymer, specifically, a U.V. curable polyurethane, can be applied to the distal section 143 and cured prior to positioning the helical coil 151 over the distal section 143. Such a thin layer of U.V. curable polyurethane or the like can prevent the second polymer layer 157 from making contact with and adhering to the distal section 143 upon application. This can relieve stresses that can build up during construction of the guidewire 140 and provide for improved handling characteristics. Also, the first polymer layer 156 may consist of a thin layer of lubricious material that prevents the second polymer layer 157 from adhering to the distal section 143 during application in order to achieve a similar result. One example of such a lubricious material is silicone oil or the like.

Many of the coating processes used to apply polymers, such as polyurethanes, can subject the helical coil 151 to mechanical stresses that can distort the configuration of the helical coil. The application of a U.V. curable adhesive as a first polymer layer 156 by dip or spray coating can eliminate this problem. Both the first polymer layer and the second polymer layer can also be made from a variety of other suitable materials such as those noted above with regard to polymer layers of other embodiments. Excepting noted differences, the features, dimensions, materials and any variations thereof for the various elements of guidewire 140 can be generally the same as the features, dimensions, materials and variations thereof of similar elements of guidewire 110 discussed above.

Figure 23:
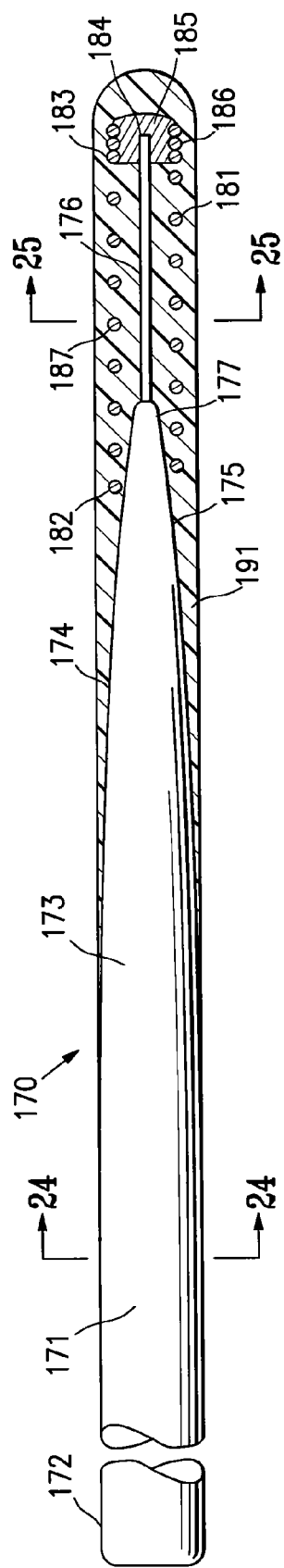
FIG. 23 is an elevational view in partial longitudinal section of a guidewire having features of the invention.
Figure 25:
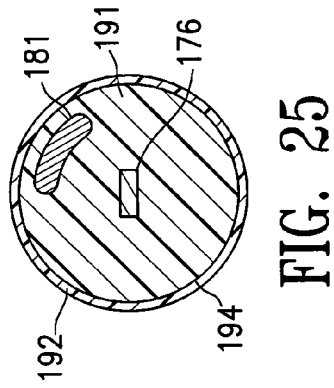
FIG. 25 is a transverse cross sectional view of the guidewire shown in FIG. 23 taken at lines 25-25 of FIG. 23.
Figure 24:
FIG. 24 is a transverse cross sectional view of the guidewire shown in FIG. 23 taken at lines 24-24 of FIG. 23.

FIGS. 23-25 show a guidewire 170 having an elongate core member 171 with a proximal section 172 and a distal section 173. The distal section 173 has a longitudinal portion 174 with a curvilinear taper 175 tapering distally to a reduced transverse dimension. A distal segment 176 is disposed at a distal end 177 of the longitudinal portion 174 which is flattened to form a more shapable distal end of the guidewire. A flexible body in the form of a helical coil 181 is disposed about the distal section 173 of the elongate core member 171 and has a proximal end 182 and a distal end 183. The helical coil 181 is attached at its distal end 183 to a distal end 184 of the distal segment 176 by a body of solder 185. The distal end 183 of the helical coil 181 has a stacked portion 186 to facilitate bonding with the body of solder 185 to the distal segment 176.

A spaced portion 187 of the helical coil 181 is disposed proximally adjacent the stacked portion 186. A polymer layer 191 is disposed about the distal section 173 of the elongate core member 171 and the helical coil 181. A lubricious coating 192 is optionally disposed on an outer surface 193 of the elongate core member and an outer surface 194 of the polymer layer. Excepting noted differences, the features, dimensions, materials and any variations thereof for the various elements of guidewire 170 can be generally the same as the features, dimensions, materials and variations thereof of similar elements of guidewires 110 and 140 discussed above.

FIGS. 26-28 show a guidewire 200 having an elongate core member 201 with a proximal section 202 and a distal section 203. The distal section 203 has a longitudinal portion 204 with a curvilinear taper 205 tapering distally to a reduced transverse dimension. A distal segment 206 is disposed at a distal end 207 of the longitudinal portion 204 which is flattened to form a more shapable distal end of the guidewire. A flexible body in the form of a helical coil 211 is disposed about the distal section 203 of the elongate core member 201 and has a proximal end 212 and a distal end 213. The helical coil 211 is attached at its distal end 213 to a distal end 214 of the distal segment 206 by a body of solder 215.

The distal end 213 of the helical coil 211 has a stacked portion 216 to facilitate bonding with the body of solder 215 to the distal segment 206. A spaced portion 217 of the helical coil 211 is disposed proximally adjacent the stacked portion 216. A polymer layer 221 is disposed about the distal section 203 of the elongate core member 201 and the helical coil 211. A lubricious coating 222 is optionally disposed on an outer surface 223 of the elongate core member 201 and an outer surface 224 of the polymer layer 221.

Disposed on the elongate core member 201 at regular intervals are radiopaque markers 225. The radiopaque markers 225 can be formed by a variety of materials and applied in various configurations. The radiopaque markers 225 can be made of a radiopaque metal, or an adhesive, polymer or ink doped with a radiopaque powder material, such as tungsten or the like. The dimensions of the radiopaque markers 225 should be suitable for accurate visualization with desired imaging techniques.

Typically, the length of the radiopaque markers can be from about 0.1 to about 5 mm, specifically about 0.5 to about 2 mm, and more specifically about 1 to about 1.5 mm. A transverse dimension of the radiopaque markers 225 can be from about 0.002 to about 0.04 inch, specifically about 0.003 to about 0.02 inch. It should be noted, however, that the transverse dimension of a radiopaque marker 225 will generally be substantially commensurate with a transverse dimension of the portion of the elongate core 111 on which the marker is disposed. Thus, the transverse dimension of the radiopaque markers 225 of guidewire 200 can vary similarly to the variation in transverse dimension of the elongate core member 111.

The axial spacing of the radiopaque markers 225 can be up to 50 mm, specifically from about 1 to about 20 mm, and more specifically about 5 to about 15 mm with a 10 mm spacing being typical. However, any desired predetermined spacing can be used. The amount of the elongate core member 201 having the radiopaque markers 225 disposed at regular intervals can be up to the entire length of the core member 201, specifically about 1 to about 20 cm of the core member, and more specifically about 2 to about 10 cm of the core member. Excepting noted differences, the features, dimensions, materials and any variations thereof for the various elements of guidewire 200 can be generally the same as the features, dimensions, materials and variations thereof of similar elements of guidewires 110, 140 and 170 discussed above.

FIGS. 29-31 show a guidewire 230 having an elongate core member 231 with a proximal section 232 and a distal section 233. The distal section 233 has a longitudinal portion 234 with a curvilinear taper 235 tapering distally to a reduced transverse dimension. A distal segment 236 is disposed at a distal end 237 of the longitudinal portion 234 which is flattened to form a more shapable distal end of the guidewire. A flexible body in the form of a helical coil 241 is disposed about the distal section 233 of the elongate core member 231 and has a proximal end 242 and a distal end 243.

The helical coil 241 can be formed of radiopaque material and has spaced portions 246 which have greater spacing between adjacent coils than adjacent non-spaced portions 247 of the helical coil 241. The spaced portions 246 provide regions of lower radiopacity relative to the radiopacity of the non-spaced portions 247. The non-spaced portions 247 may be stacked, i.e. adjacent coils touching or nearly touching each other, or may be merely spaced less than the coils of the spaced portions 246.

A radiolucent material may be disposed in the spaced portions of the helical coil. The radiolucent material is optional, but may be desirable to facilitate securing of the helical coil 241 to the elongate core member 231 and the distal segment 236. A first radiolucent body of solder 251 and a second radiolucent body of solder 252 are shown securing the helical coil 241 to the distal segment 236. The first and second bodies of radiolucent solder 251 and 252 can be made of common silver solder as is known in the art for securing guidewire components, however, any suitable bonding material can be used.

A polymer layer 253 is disposed about the distal section 233 of the elongate core member 231 and the helical coil 241. A lubricious coating 254 is optionally disposed on an outer surface 255 of the elongate core member 231 and an outer surface 256 of the polymer layer 253. The axial length and spacing of the spaced portions 246 or non-spaced portions 247 of the helical coil 241 can be similar to the length and axial spacing of the radiopaque markers 225 of guidewire 200 discussed above. Excepting noted differences, the features, dimensions, materials and any variations thereof for the various elements of guidewire 230 can be generally the same as the dimensions, materials and variations thereof of similar elements of guidewire 110 discussed above.

Figure 32:
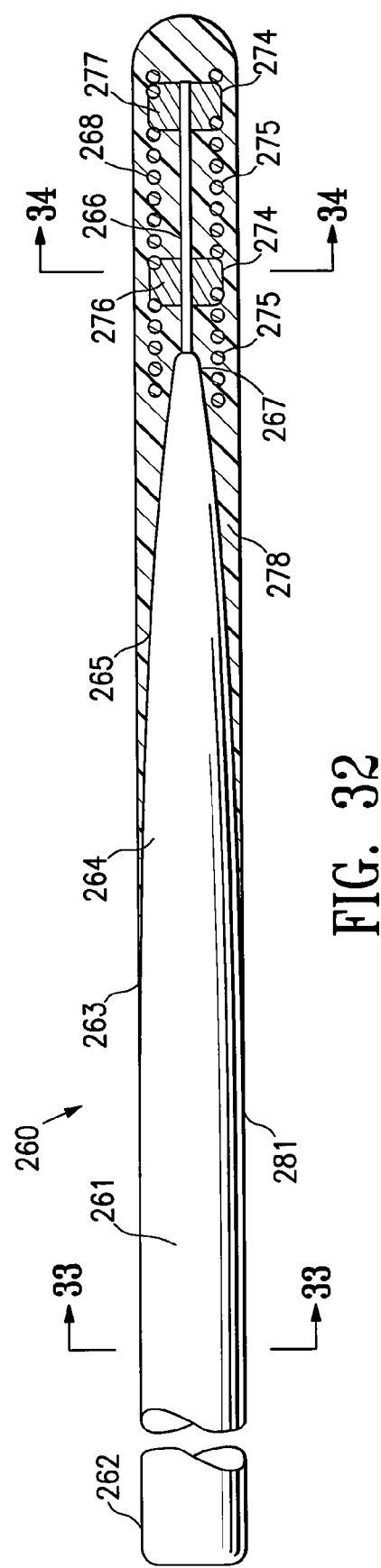
FIG. 32 is an elevational view in partial longitudinal section of a guidewire having features of the invention.
Figure 34:
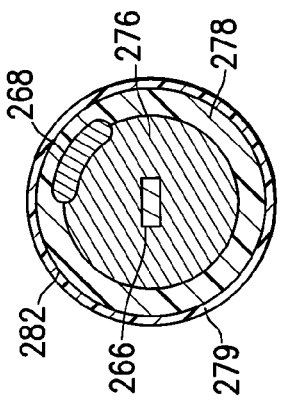
FIG. 34 is a transverse cross sectional view of the guidewire shown in FIG. 32 taken at lines 34-34 of FIG. 32.
Figure 33:
FIG. 33 is a transverse cross sectional view of the guidewire shown in FIG. 32 taken at lines 33-33 of FIG. 32.

FIGS. 32-34 show a guidewire 260 having an elongate core member 261 with a proximal section 262 and a distal section 263. The distal section 263 has a longitudinal portion 264 with a curvilinear taper 265 tapering distally to a reduced transverse dimension. A distal segment 266 is disposed at a distal end 267 of the longitudinal portion 264 which is flattened to form a more shapable distal end of the guidewire. A flexible body in the form of a helical coil 268 is disposed about the distal section 263 of the elongate core member. The helical coil 268 is formed of a radiolucent material and has spaced portions 274 which have greater spacing between adjacent coils than adjacent non-spaced portions 275 of the helical coil 268. The non-spaced portions 275 may be stacked, i.e. adjacent coils touching or nearly touching each other, or may merely be spaced less than the adjacent coils of the spaced portions 274.

A first radiopaque body of solder 276 and a second radiopaque body of solder 277 are shown securing the helical coil 268 to the distal portion 263 of the elongate core member. The first and second bodies of radiopaque solder 276 and 277 can be made of gold solder or any other suitable bonding material with radiopaque properties. Any number of radiopaque bodies of solder can be disposed in a like number of spaced portions 274 of a helical coil 268 in order to form a longitudinal array of radiopaque markers at regular intervals to facilitate measurement of intracorporeal structures during a clinical procedure.

Typically, the guidewire 260 will have between about 2 to about 20 such radiopaque makers on the distal section 263. The axial length and spacing of the radiopaque bodies of solder 276 and 277 can be similar to or the same as the axial length and spacing of the radiopaque markers 225 of guidewire 200 discussed above. A polymer layer 278 is disposed about the distal section 263 of the elongate core member 261 and the helical coil 268. A lubricious coating 279 is optionally disposed on an outer surface 281 of the elongate core member 261 and an outer surface 282 of the polymer layer 278. Excepting noted differences, the features, dimensions, materials and any variations thereof for the various elements of guidewire 260 can be generally the same as the features, dimensions, materials and variations thereof of similar elements of guidewire 110 discussed above.

FIGS. 35 and 36 show a polymer tubular member 284 having a plurality of radiopaque longitudinal segments 285 and radiolucent longitudinal segments 286. The polymer tubular member 284 can be extruded as a single piece, or may be made from individual segments which are bonded or fused together. The length and spacing of the segments 285 and 286 can be chosen to give a desired demarcation of structures within a patient's body during a procedure. Typically, the polymer tubular member 284 is made of a polymer such as polyurethane that has been doped with a radiopaque material, such as tungsten powder or the like, in the radiopaque longitudinal segments 285. The axial length and spacing of the segments 285 and 286 can be the same or similar to the axial length and spacing of the radiopaque markers 225 of guidewire 200 discussed above.

FIGS. 37 and 38 show a guidewire 290 having an elongate core member 291 with a proximal section 292 and a distal section 293. The distal section 293 has a curvilinear taper 294 tapering distally to a reduced transverse dimension. A flexible body in the form of a polymer tubular member 295 is disposed about the distal section 293 of the elongate core member 291 and is optionally secured by a suitable adhesive thereto. The polymer tubular member 295 has a plurality of radiopaque longitudinal segments 296 and radiolucent longitudinal segments 297. The polymer tubular member 295 can be extruded as a single piece, or may be made from individual segments which are bonded or fused together.

The features, dimensions and materials of the polymer tubular number 295 can be the same as or similar to the features, dimensions and materials of the polymer tubular member 284 discussed above and should be chosen to give a desired demarcation of structures within a patient's body during a procedure. A polymer layer 298 is disposed about the distal section 293 of the elongate core member 291 and the polymer tubular member 295. A lubricious coating 299 is optionally disposed on an outer surface 301 of the elongate core member 291 and an outer surface 302 of the polymer layer 298. Excepting noted differences, the dimensions, materials and any variations thereof for the various elements of guidewire 290 can be generally the same as the dimensions, materials and variations thereof of similar elements of guidewire 110 discussed above.

FIG. 39 illustrates a guidewire 310 having an elongate core member 311 with a proximal section 312 and a distal section 313. The distal section 313 has a longitudinal portion 314 which tapers distally to a reduced transverse dimension. Optionally, there is a flattened shapable distal segment 315 which can extend from a distal end 314A of the longitudinal portion 314. The distal end 315A of the segment 315 is secured to a distal end 316A of a flexible body 316 with adhesive forming a rounded distal tip 317. Excepting noted differences, the dimensions, materials and any variations thereof for the various elements of guidewire 310 can be generally the same as the dimensions, materials and variations thereof of similar elements of guidewire 110 discussed above.

Flexible body 316 is disposed about and secured to the distal section 313 of the core member 311 and has at least one polymer layer 316B. The polymer layer 316B may be applied to the distal core section by the methods described above with regard to applying polymer layers or any other suitable means that produces a smooth continuous surface. Suitable polymer materials for the polymer layer 316B can include the materials previously discussed with regard to polymer layer 126 discussed above. The thickness of the polymer layer 316B can range from about 0.0005 inch to about 0.0060 inch, preferably about 0.0010 inch to about 0.0030 inch. The polymer layer 316B can be about 5 to about 35 cm in length, extending proximally from the rounded distal tip 317. A radiopaque layer 316C is disposed about the distal section 113 of the elongate core 111. The radiopaque layer 316C is shown as intermittent in an axial direction and may be made of a helical coil or bands of radiopaque material.

As shown in FIGS. 40A-41, the flexible body 316 can be made of a first polymer layer 318 disposed about the distal section 313 of the elongate core 311 and a second polymer layer 319 disposed about the first polymer layer 318. A radiopaque layer 320A is disposed between the first polymer layer 318 and the second polymer layer 319. Radiopaque layer 320A is illustrated as being intermittent in an axial direction and may be made of a helical ribbon coil or bands of a radiopaque material. FIG. 42 illustrates another embodiment where the radiopaque layer 320B is continuous in an axial direction. Radiopaque layer 320B is sandwiched between first polymer layer 318 and second polymer layer 319. The thickness of the radiopaque layers 316C, 320A and 320B can range from about 0.0005 inch to about 0.0040 inch, preferably from about 0.0015 inch to about 0.0025 inch.

FIGS. 40A-41 illustrate an embodiment where the flexible body 316 has a radiopaque layer 320A formed of radiopaque elements 321 which are spaced apart a predetermined distance in an axial direction. The radiopaque elements 321 are preferably in the form of bands, positioned circumferentially around the elongate core 311. The radiopaque elements 321 can have a thickness from about 0.0005 inch to about 0.0040 inch, specifically from about 0.0015 inch to about 0.0025 inch. The radiopaque elements 321 can be about 0.5 to 5 mm in width, specifically 1 to 2 mm in width, and can be spaced about 0.2 to about 2 cm apart in an axial direction. The radiopaque layer 320A may be in the form of a stretched helical ribbon being open wound with turns not touching each other and the thickness of the helical ribbon can be from about 0.0005 inch to about 0.0040 inch, preferably from about 0.0015 inch to about 0.0025 inch. A helical ribbon suitable for the radiopaque layer 320A can be about 0.5 to 2 mm wide and the turns of the helical ribbon can be about 1 to about 15 mm apart.

The radiopaque layers 316C, 320A and 320B can be formed from radiopaque metals such as platinum, gold, iridium, palladium, tantalum, tungsten, or alloys thereof. Conventional non-metallic radiopaque materials may also be used. Additionally the radiopaque layers 316C, 320A and 320B may be made of a polymer doped with a radiopaque material, such as those discussed above.

The flexible body 316 may be applied directly to the distal section 313 of the elongate core member 311 or they may be first formed elsewhere and then applied to the elongate core member by a suitable attachment means, preferably by adhesive or by shrink fitting. The elongate core 311 member can be formed of a strong, yet flexible material, such as stainless steel, NITINOL, MP35N, L650, Elgiloy or other materials, or combinations thereof.

In general, the overall length of the guidewire 310 may range from about 80 to about 320 cm, preferably about 160 to about 200 cm for coronary use. The guidewire 310 may be produced in commercially standard lengths of 175, 190 and 300 cm. The distal section 113 of the guidewire 310 can be about 1 to about 30 cm, preferably about 2 to about 10 cm in length. The outer diameter of the guidewire may vary depending upon use, but typically is about 0.008 to about 0.035 inch (0.2 to 0.9 mm). The number, lengths and diameters of the tapers may likewise vary.

As discussed above, it can be desirable to have the polymer layer or layers of the embodiments discussed above applied with an apparatus and process that produces a smooth continuous outer surface.

FIGS. 43-46 illustrate such a polymer coating apparatus 410 for applying a polymer coating 411 to an elongate intracorporeal device 412 such as the guidewire embodiments described above. A guide tube assembly 413 is removably secured to a guide tube assembly mount 414. The guide tube assembly mount 414 is secured to a mounting surface 415, which is typically an even vertical surface, but which can have any desired configuration or orientation. A heater member 416 is secured in thermal communication with a guide tube housing 417 of the guide tube assembly 413 and serves to supply heat energy to a desired portion of the guide tube assembly 413. The guide tube assembly 413 includes a guide tube housing 417 which has an input end 418 and an output end 419. The output end 419 has a threaded portion 422 and the input end 418 has a retainer lip 423. A retainer cap 424 is threaded onto the threaded portion 422 of the output end 419 of the guide tube housing 417.

The guide tube housing 417 can be made of a conductive material such as stainless steel, a machineable insulative material such as Vespel® or any other suitable material. As shown in FIG. 44, within the guide tube housing 417, a guide tube 425 having an input end 426, an output end 427 and a guide chamber 428 disposed within the guide tube 425 has the input end 426 of the guide tube 425 disposed against the retainer lip 423 of the guide tube housing 417. A die 431 having an input end 432 and an output end 433 is disposed within the guide tube housing 417 with the input end 432 of the die 431 against the output end 427 of the guide tube 425. An optional centering insert 434 having an input end 435 and an output end 436 is disposed within the guide tube housing 417 with the input end 435 of the centering insert 434 against the output end 433 of the die 431. The retainer cap 424 with a center hole 437 is threaded onto the threaded portion 422 of the guide tube housing 417 to hold the guide tube 425, die and centering insert 434 within the guide tube housing 417.

In one embodiment, the guide tube 425 has a length of about 0.5 to about 5 inch, specifically about 1.0 to about 3.0 inch. The guide tube 425, die 431 and centering insert 434 can have an outer diameter of about 0.03 to about 0.2 inch, specifically about 0.05 to about 0.1 inch. The guide tube 425 of the embodiment can have a wall thickness of about 0.005 to about 0.015 inch. In other embodiments, the length, outer diameter and wall thickness of the guide tube 425 can vary significantly from the dimensions given above to suit the desired application. The guide tube 425, die 431 and centering insert 434 can be disposable and made from a high temperature polymer such as PI, PTFE, LCP or PEEK.

Figure 43:
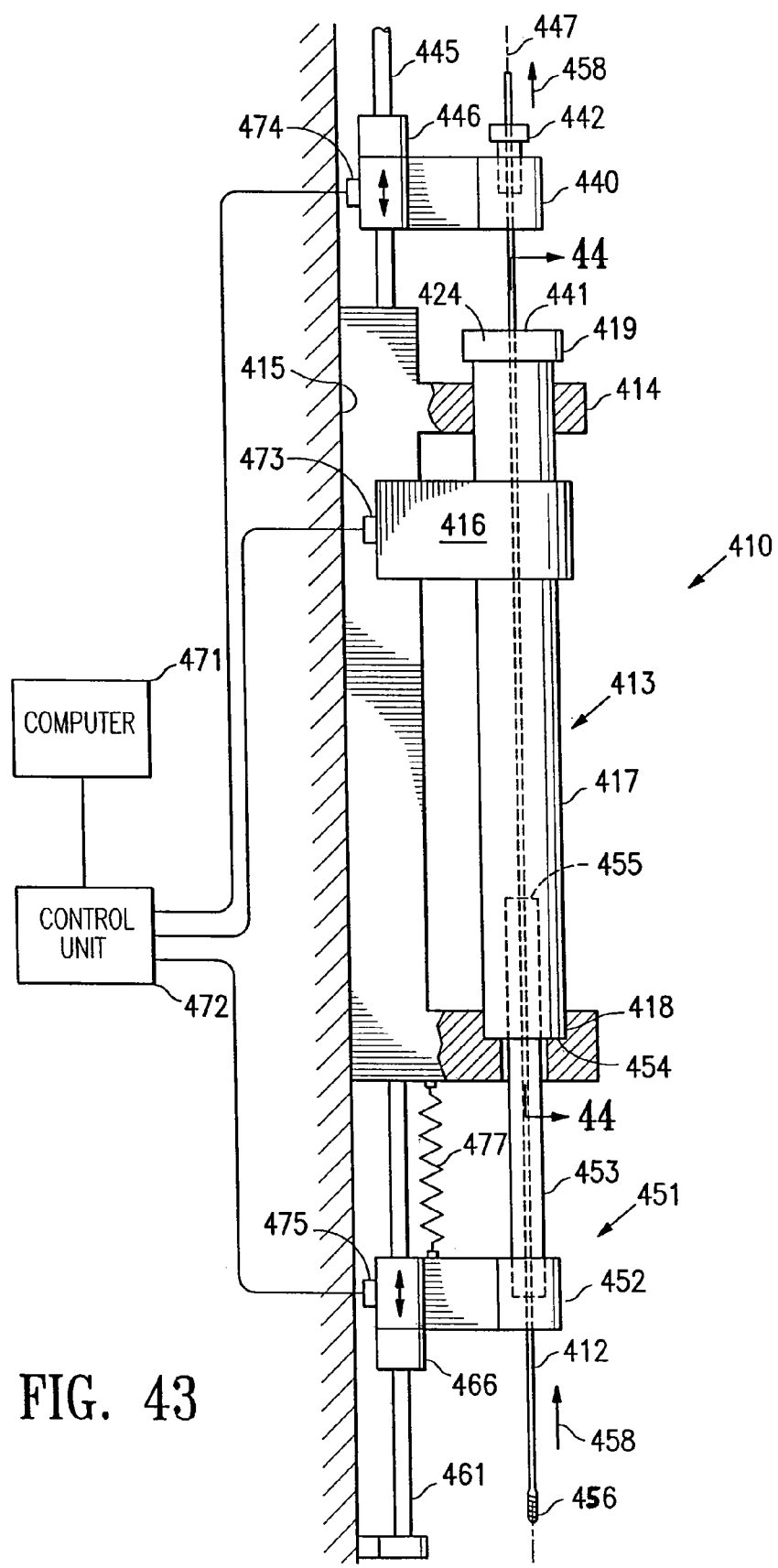
FIG. 43 is an elevational view in partial section of an apparatus for applying a polymer coating to an elongate intracorporeal device having features of the invention.

As best shown in FIG. 43, a puller 440 is disposed adjacent an output end 441 of the guide tube assembly 413 and has a clamp 442 aligned with the longitudinal axis 443 of an inner lumen 444 of the die 431 for temporarily securing the elongate intracorporeal device 412 to the puller 440. The clamp 442 temporarily secures a desired portion of the elongate intracorporeal device 412 to the puller 440 such that the elongate intracorporeal device 412 is centered within the inner lumen 444 of the die 431. The puller 440 is slidably disposed on a puller track 445 and has motor 446 which mechanically engages the puller track 445 and moves the puller 440 along a longitudinal axis 447 of the guide tube assembly 413.

A cartridge advancement mechanism 451 consisting of a push tube actuator 452 and a push tube 453 is disposed adjacent an input end 454 of the guide tube assembly 413. The push tube actuator 452 is mechanically coupled to the push tube 453 with the push tube 453 having a contact end 455 and an actuator end 456. The push tube 453 is configured to have the contact end 455 slidably disposed within the guide chamber 428 of the guide tube 425 and apply force to an extrudable polymer cartridge 457 disposed within the guide chamber 428 in a direction of extrusion. The direction of extrusion is defined to be from the input end 454 of the guide tube assembly 413 to the output end 441 of the guide tube assembly 413 as indicated by arrows 458.

The push tube actuator 452 is slidably disposed on a push tube actuator track 461 such that a longitudinal axis 462 of an inner lumen 463 of the push tube 453 is aligned with the longitudinal axis 443 of the die 431 and longitudinal axis 464 of an inner lumen 465 of the extrudable polymer cartridge 457. A push tube actuator motor 466 is disposed on the push tube actuator 452 and mechanically coupled to the push tube actuator track 461 so as to enable the motor 466 to axially translate the push tube actuator 452 on the push tube actuator track 461 along a longitudinal axis 447 of the guide tube assembly 413.

The elongate intracorporeal device 412 is disposed within an inner lumen 467 of the centering insert 434, the extrusion orifice 468 of the die 431, the inner lumen 465 of the extrudable polymer cartridge 457 and the inner lumen 463 of the push tube 453. The elongate intracorporeal device 412 is also shown as being disposed along the longitudinal axis 447 of the guide tube assembly 413. Other configurations may be used where the elongate intracorporeal device 412 is offset from the longitudinal axis 447 of the guide tube assembly 413.

A computer 471 is in electrical communication with an electronic control unit 472 which is in electrical communication with a temperature sensor 473 disposed in thermal communication with the heater member 416, a puller position indicator 474 disposed on the puller 440, and a push tube actuator position indicator 475 disposed on the push tube actuator 452. The temperature sensor 473 provides an electrical signal to the computer 471 indicating the temperature of the heater member 416. The puller position indicator 474 provides an electrical signal to the computer 471 indicating the position of the puller 440 relative to the output end 441 of the guide tube assembly 413. The push tube actuator position indicator 475 provides an electrical signal to the computer 471 indicating the position of the push tube actuator 452 relative to the input end 454 of the guide tube assembly 413. In addition, the computer 471 is electrically coupled to the control unit 472 such that a signal from the computer 471 can control the amount of power to the heater member 416, the speed and direction of translation of the puller 440 and the speed and direction of translation of the push tube actuator 452.

In this way, the computer 471 can be programmed to repeatably control the temperature of the heater member 416, the rate of pull of the elongate intracorporeal device 412 through the guide tube assembly 413 and the rate of feed of the extrudable polymer cartridge 457 into the guide chamber 428 in the direction of extrusion. This enables the computer 471 to repeatably control the entire coating process for consistent coating results. The computer 471 may be a standard personal computer, or any suitable substitute such as a custom integrated circuit or the like. In addition, the function of the computer 471 could be carried out with standard analog circuitry of suitable configuration that would provide a desired and repeatable heater member 416 temperature, rate of pull of the puller 440 and rate of feed of the push tube actuator 452.

In use, the retainer cap 424 is removed from the guide tube housing 417. The guide tube 425 is loaded into the guide tube housing 417 from the output end 419 of the guide tube housing 417 until the input end 426 of the guide tube 425 contacts the retainer lip 423 of the guide tube housing 417 and the contact end 455 of the push tube 453 enters the guide tube chamber 428 at the input end of the guide tube 425. The extrudable polymer cartridge 457 is then loaded into the guide chamber 428 at the output end of the guide tube 425 until it contacts the contact end 455 of the push tube 453. Next, the die 431 is loaded into the guide tube housing 417 with the input end 432 of the die 431 adjacent the output end 427 of the guide tube 425. The centering insert 434 is then loaded into the guide tube housing 417 with the input end 435 of the centering insert 434 adjacent the output end 433 of the die 431. The retainer cap 424 is then replaced which confines the guide tube 425, extrudable polymer cartridge 457, die 431 and centering insert 434 within the guide tube housing 417.

The elongate intracorporeal device 412 is then inserted through the inner lumen 467 of the centering insert 434, the extrusion orifice 468 and inner lumen 444 of the die, the inner lumen 465 of the extrudable polymer cartridge 457, and at least a portion of the inner lumen 463 of the push tube 453. The elongate intracorporeal device 412 is then temporarily secured to the puller 440 by the clamp 442. The coating cycle is then started by supplying power to the heater member 416 which heats a desired portion of the die 431, guide tube 425 and extrudable polymer cartridge 457 which are adjacent the heater member 416.

Thermal energy from the heater member 416 may be coupled to the die 431 alone, the die 431 and the output end 427 of the guide tube 425 or the die 431 and any desired portion of the guide tube 425. Also, it may be useful in some embodiments to generate a temperature gradient along the centering insert 434, die 431 and guide tube 425. In one embodiment, it is preferable to concentrate most of the thermal energy on the die 431 and output end 427 of the guide tube 425.

As thermal energy is transferred to the extrudable polymer cartridge 457, it can begin to soften or melt at a melt zone 457A. When the portion of the extrudable polymer cartridge 457 adjacent the die 431 approaches a desired temperature or viscosity or both, force in the direction of extrusion is applied to the extrudable polymer cartridge 457. This pushes the melted or softened polymer material in the melt zone 457A of the extrudable polymer cartridge 457 into the input end 432 and inner lumen 444 of the die 431 and onto the elongate intracorporeal device 412. When the force in the direction of extrusion is initiated on the extrudable polymer cartridge 457, the elongate intracorporeal device 412 is simultaneously advanced in the direction of extrusion as the extrudable polymer cartridge 457 is heated, melted, and forced into the die 431. The melted extrudable polymer cartridge 457 is applied to the moving elongate intracorporeal device 412 in a radially inward direction as indicated by arrows 457B. As shown in FIG. 44, the extrudable polymer cartridge 457 is applied evenly at the melt zone 457A from all directions as indicated by arrows 457B. The force of this evenly distributed inward radial force helps maintain the concentricity of the polymer coating 411 if the lumen of the extrudable polymer cartridge is concentric with the longitudinal axis 464 of the extrudable polymer cartridge 457 and longitudinal axis 443 of the die 431. The coating process is carried out continuously until a desired portion of the elongate intracorporeal device 412 has been coated. The process may be terminated by exhaustion of the extrudable polymer cartridge 457, cessation of the force in the direction of extrusion on the extrudable polymer cartridge, or passage of an extremity 476 of the elongate intracorporeal device 412 through the die 431.

In the embodiment of the polymer coating apparatus 410 shown in FIGS. 43-46, the force in the direction of extrusion on the extrudable polymer cartridge 457 is applied by the contact end 455 of the push tube 453 which is mechanically coupled to the push tube actuator 452. One alternative to the push tube actuator 452 is to apply a substantially constant force in the direction of extrusion on the push tube 453 with an optional constant force spring 477. The constant force spring 477 may be secured to any suitable portion of the push tube 453, push tube actuator 452, guide tube assembly mount 414, or mounting surface 415. A suitable trigger mechanism can be used to initiate the force from the constant force spring 477 in the direction of extrusion at the appropriate time in the coating cycle.

When the coating cycle is finished, the elongate intracorporeal device 412 is removed from the guide tube assembly 413 and the puller 440. The retainer cap 424 of the guide tube housing 417 is removed as well as the spent die 431, centering insert 434, guide tube 425 and extrudable polymer cartridge 457. The push tube 453 is then reset to its original position and a new guide tube 425, extrudable polymer cartridge 457, die 431 and centering insert 434 loaded into the guide tube housing 417. It may be possible to reuse the die 431, guide tube 425 or centering insert 434. Also, the new guide tube 425, die 431 and extrudable polymer cartridge 457 may be loaded into the guide tube housing 417 in one modular unit or subassembly in order to lessen the time between coating cycles.

The temperature range of the heater member 416 used for the process of the polymer coating apparatus 410 can vary significantly depending on the desired result, size and material composition of the elongate intracorporeal device 412 and material composition of the extrudable polymer cartridge 457. For coating an elongate intracorporeal device 412 consisting of a guidewire, in order to yield a finished outer diameter of about 0.012 to about 0.016 inch, a temperature range of about 340 to about 390 degrees Fahrenheit, specifically about 350 to about 380 degrees Fahrenheit is typical if using polyurethane for the extrudable polymer cartridge 457 material.

As the temperature of the heater member 416 is changing as the coating process is started, it may be desirable to trigger axial movement of the elongate intracorporeal device 412 in the direction of extrusion just prior to reaching the desired target temperature. For example, if the ultimate target temperature of the heater member 416 is about 365 degrees Fahrenheit, then the puller 440 may be triggered by programming of the computer 471 to start the puller 440 moving in the direction of extrusion when the heater member 416 reaches a temperature of about 362 degrees Fahrenheit.

The rate of speed of pull of the elongate intracorporeal device 412 through the guide tube assembly 413 can vary considerably depending on many factors including the size and durability of the elongate intracorporeal device 412, the temperature of the heater member 416 and the material of the extrudable polymer cartridge 457. For the example given above, with an elongate intracorporeal device 412 of stainless steel having a desired finish outer diameter of about 0.012 to about 0.016 inch, using polyurethane for the extrudable polymer cartridge 457, a typical rate of pull can be from about 0.25 to about 1.0 cm/second for durable portions of the member 412, and about 0.05 to about 0.15 cm/second for more fragile portions of the member 412, such as portions of the elongate intracorporeal device 412 covered by a helical coil which is subject to mechanical deformation. The force applied to the extrudable polymer cartridge 457 by the push tube 453 via the push tube actuator 452 can be from about 0.5 to about 10 pounds, specifically about 1.0 to about 2.0 pounds.

In another embodiment, the cartridge advancement mechanism 451, described above as consisting of a push tube actuator 452 coupled to a push tube 453 can be replaced with a substantially constant force spring coupled to the push tube so as to apply a substantially constant force in the direction of extrusion on the extrudable polymer cartridge 457 during the coating process. The amount of force can be similar to the forces noted above with regard to the push tube actuator 452 embodiment.

Figure 47:
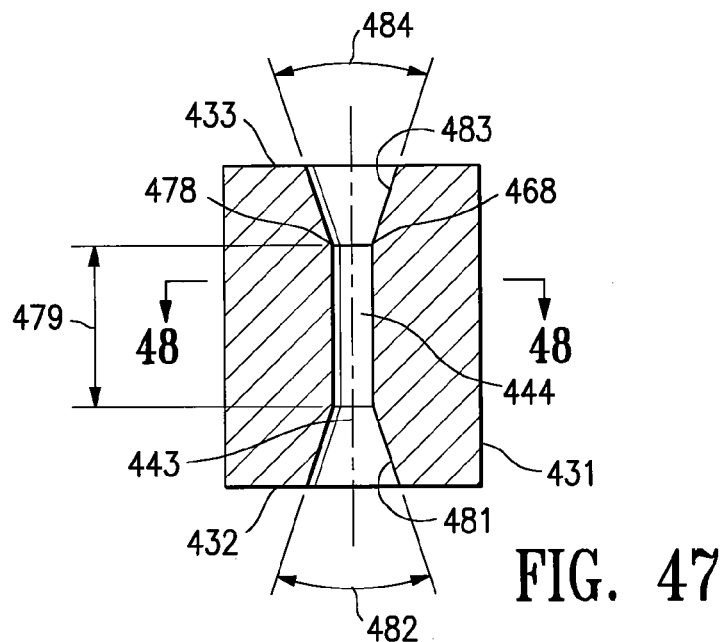
FIG. 47 is an elevational view in longitudinal cross section of the die in the guide tube assembly shown in FIGS. 42-46, having features of the invention.
Figure 48A:
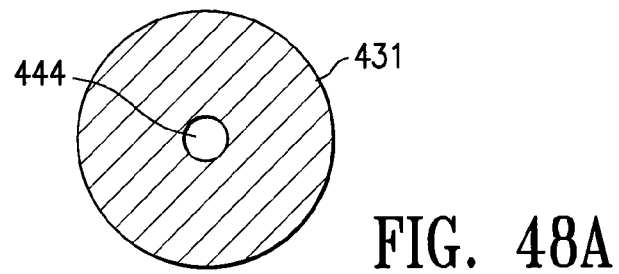
FIGS. 48A-48C are transverse cross sectional views of the die shown in FIG. 47 taken along lines 48-48 in FIG. 47.
Figure 48B:
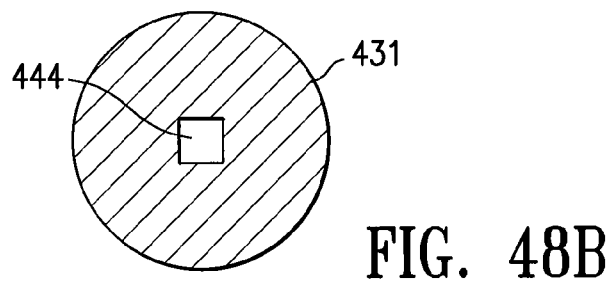
Figure 48C:
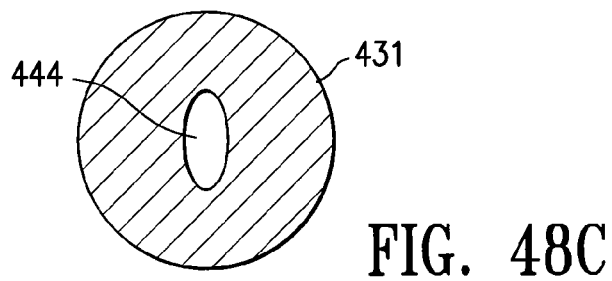

FIGS. 47-48C illustrate an enlarged view of the embodiment of the die 431 shown in FIGS. 44 and 47. The die 431 can be made from a variety of materials, including high temperature polymers such as PI, PTFE, LCP and PEEK. The die 431 can also be made from metal or any other suitable material. The die 431 has an input end 432, an output end 433 and an inner lumen 444. An extrusion orifice 468 is disposed at an output extremity 478 of the inner lumen 444. The length 479 of the inner lumen 444 of the die 431 can vary significantly depending on the desired result and numerous other factors. A typical length of the inner lumen 444 can range from about 0.02 to about 0.5 inch, specifically about 0.05 to about 0.08 inch. A transverse dimension of the inner lumen 444 and extrusion orifice 468 of the die 431 can be from about 0.01 to about 0.25 inch, specifically about 0.011 to about 0.015 inch.

The die 431 has an outer transverse dimension similar to an inner transverse dimension of the guide tube. An input taper 481 at the input end 432 of the die 431 has an input taper angle 482. An optional output taper 483 at the output end 433 of the die 431 has an output taper angle 484. Output taper angle 484 and input taper angle 482 can be from about 180 degrees, i.e. a flat cut end with no taper, to about 15 degrees, specifically from about 35 to about 45 degrees, and more specifically, from about 36 to about 40 degrees. Although the extrusion orifice 468 of the die 431 shown in FIG. 47 has a round cross section as shown in FIG. 48A, the cross section of the extrusion orifice 468 can have any desired configuration or shape such as the square configuration shown in FIG. 48B or the elliptical configuration shown in FIG. 48C. Any other suitable extrusion orifice 468 configuration or cross sectional shape can be used to achieve a desired result.

Figure 49:
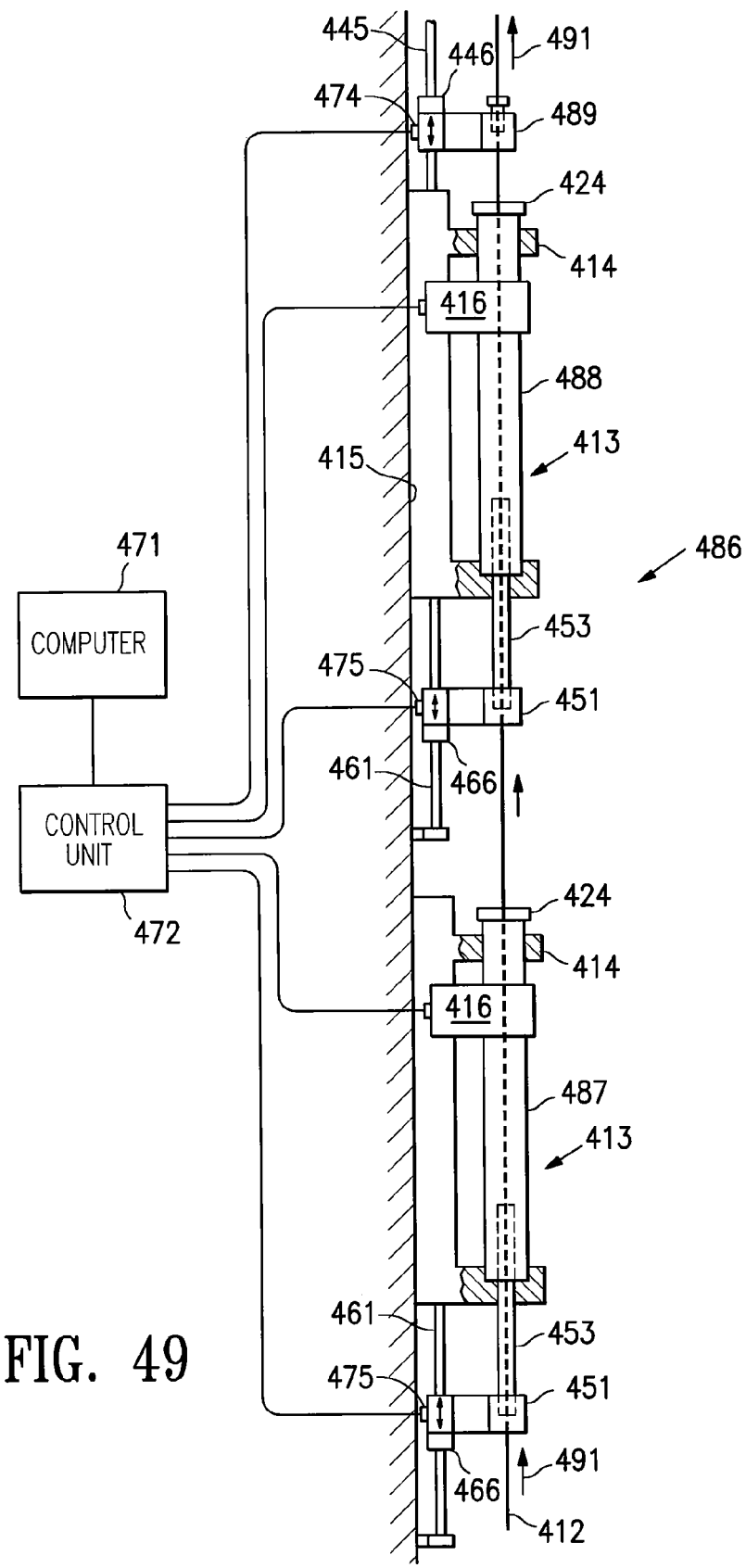
FIG. 49 is an elevational view in partial section of a tandem apparatus for applying a polymer coating to an elongate intracorporeal device having features of the invention.

FIG. 49 illustrates a tandem polymer coating apparatus 486 having a first polymer coating apparatus 487 in line with a second polymer coating apparatus 488. The various components of the first and second polymer coating apparatus 487 and 488 can have components similar to the components of the polymer coating apparatus 410 of FIGS. 43-46, and are numbered accordingly. A single puller 489 can be used for the tandem polymer coating apparatus 486. By using a tandem coating apparatus 486, multiple layers of polymer coating may be applied to a single elongate intracorporeal device 412 by drawing the elongate intracorporeal device 412 through the first and second polymer coating apparatus 487 and 488 in serial in a direction of extrusion indicated by arrow 491. Multiple coatings may be applied so as to be axially coextensive on the elongate intracorporeal device 412. Multiple coatings may also be applied to separate axial portions of an elongate intracorporeal device 412 or such that the multiple coatings overlap each other by a desired amount. Although FIG. 49 depicts a tandem coating apparatus 486 having two polymer coating apparatus 487 and 488 in serial, any desired number of polymer coating apparatus may be used.

Figure 50:
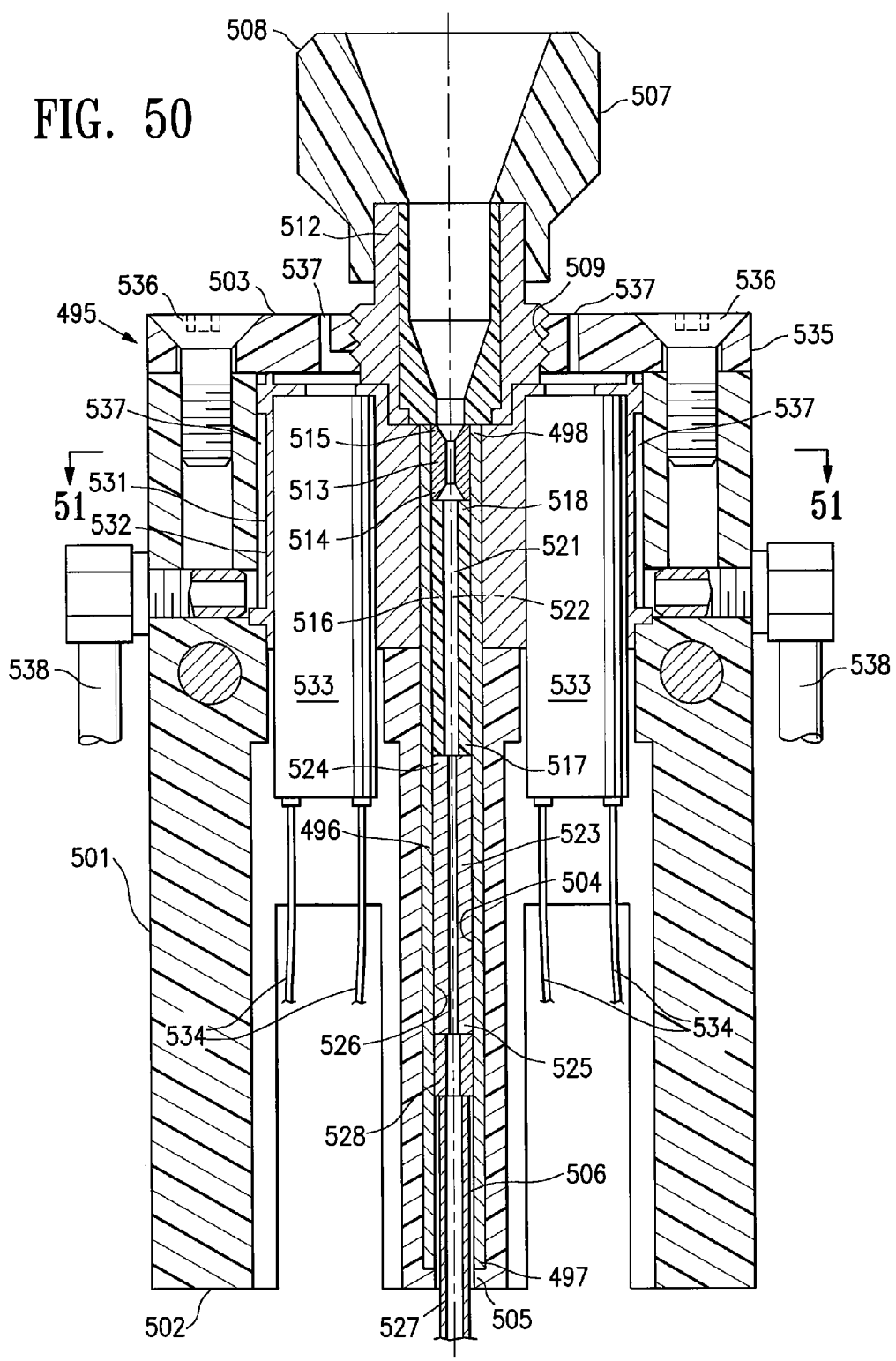
FIG. 50 illustrates an elevational view in section of a guide tube assembly having features of the invention.
Figure 51:
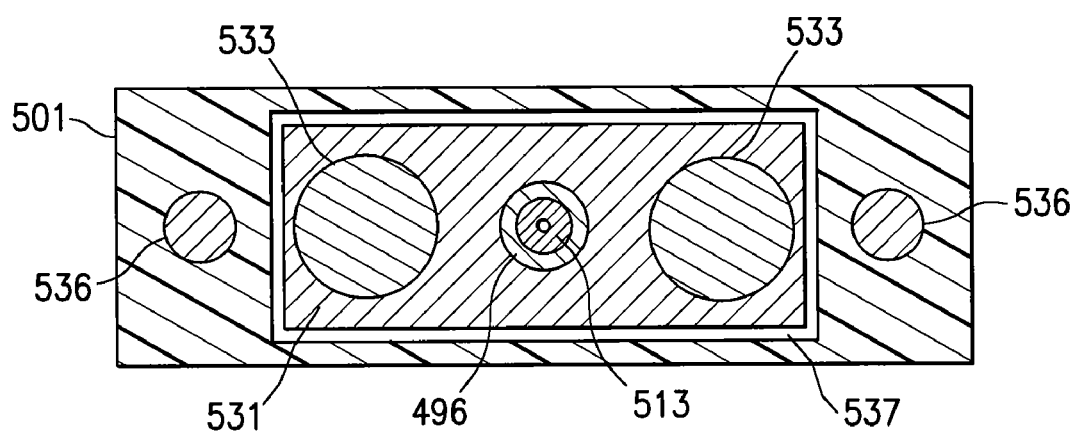
FIG. 51 is a transverse cross sectional view of the guide tube assembly of FIG. 50 taken along lines 51-51 in FIG. 50.

FIGS. 50 and 51 illustrate another embodiment of a guide tube assembly 495 having features of the invention. The guide tube assembly 495 includes a guide tube 496 having an input end 497 and an output end 498 disposed partially within a guide tube housing 501. The guide tube 496 can be made from a variety of polymer materials, specifically, high temperature polymer materials such as PI, PTFE, LCP and PEEK. The guide tube housing 501 has an input end 502 and an output end 503. The guide tube housing 501 also has a central inner lumen 504 which is configured to accept the guide tube 496. The central inner lumen 504 of the guide tube housing 501 has a retainer lip 505 at the input end 502 of the guide tube housing 501 which is configured to prevent the guide tube 496 from exiting the input end 502 of the guide tube housing 501 without blocking or interfering with a guide chamber 506 disposed within the guide tube 496. The central inner lumen 504 of the guide tube housing 501 is capped at the output end 503 with a retainer cap 507. The retainer cap 507 has a retainer cap top 508, a threaded portion 509 and a retainer cap insert 512. The retainer cap 507, when secured to the guide tube housing 501, confines the output end 498 of the guide tube 496 within the central inner lumen 504 of the guide tube housing 501.

Disposed within the output end 498 of the guide tube 496 is a die 513 which has an input end 514 and an output end 515 and which can have the same configuration, dimensions and materials as the die 431 shown in FIGS. 47-48C. Disposed within the guide tube 496 adjacent the input end 514 of the die 513 is an extrudable polymer cartridge 516 having an input end 517 and an output end 518. An inner lumen 521 extends along a longitudinal axis 522 of the extrudable polymer cartridge 516. A push tube 523 having a contact end 524 and an actuator end 525 is disposed within a guide chamber 526 of the guide tube 496 with the contact end 524 adjacent the input end 517 of the extrudable polymer cartridge 516. A push tube actuator rod 527 with an actuator rod tip 528 is disposed partially within the guide chamber 526 with the actuator rod tip 528 disposed adjacent the actuator end 525 of the push tube 523.

A heater member 531 is disposed within the guide tube housing 501 about the output end 498 of the guide tube 496. The heater member 531 has a heater member housing 532, heater rods 533 and heater lead wires 534 which supply power to the heater rods 533. The heater member housing 532 can be made from stainless steel or any other suitable material which can withstand high temperatures. It may be desirable to use a material which readily conducts heat for the heater member housing 532. The heater member 531 is held in place within the guide tube housing 501 by a guide tube housing cap 535 disposed at the output end 503 of the guide tube housing 501.

The guide tube housing cap 535 can be secured to the guide tube housing 501 by screws 536. The guide tube housing 501 has cooling air channels 537 disposed within the housing 501 fed by air lines 538 to allow air to be circulated about the heater member 531 and cool the heater member 531 after a polymer coating process has been completed and a new guide tube 496, die 513, extrudable polymer cartridge 516 and push tube 523 inserted into the guide tube assembly 495. The optionally disposable components of the guide tube assembly 495 including the guide tube 496, die 513, extrudable polymer cartridge 516 and push tube 523 may be replaced separately, or all at once as a modular subassembly.

The guide tube 496, die 513, extrudable polymer cartridge 516 and push tube 523 are replaced by removing the retainer cap 507, withdrawing the spent guide tube 496, die 513, extrudable polymer cartridge 516 and push tube 523, and then replacing a new guide tube, die, extrudable polymer cartridge and push tube. The retainer cap 507 is then secured to the guide tube housing 501. The guide tube housing 501, guide tube housing cap 535 and retainer cap top 508 can all be made from a high strength machineable polymer insulator, such as Vespel® which is a polyimide resin based composite, or any other suitable material. An insulative material can be used for the guide tube housing 501, guide tube housing cap 535 and retainer cap top 508 in order to facilitate handling by the operators of the device who must handle the various components of the polymer coating apparatus during its operation.

The guide tube assembly 495 shown in FIGS. 50 and 51 is used in a manner similar to that discussed above with regard to the embodiment of the guide tube assembly 413 shown in FIGS. 43-46. The coating process parameters discussed above with regard to the embodiment of the guide tube assembly 413 shown in FIGS. 43-46, including, but not limited to, temperatures, pull speeds, rates of feed, forces on the extrudable polymer cartridge 457, and the like, and structures and alternative structures used to implement those parameters, can all be the same or similar for the embodiment of the guide tube assembly 495 shown in FIGS. 50 and 51.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire comprising:
   an elongate core member having a proximal section and a distal section with a longitudinal portion which tapers distally to a reduced transverse dimension; wherein the taper creates a substantially linear change in stiffness of the core member over a length thereof; and
   a tubular polymer member disposed about the distal section of the elongate core member having a plurality of longitudinal segments with at least one of the longitudinal segments being radiopaque and at least one of the segments being radiolucent.

2. The guidewire of claim 1 wherein the longitudinal portion has a curvilinear taper.

3. The guidewire of claim 1 wherein the longitudinal portion has a length of about 10 to about 25 cm.

4. The guidewire of claim 1 further comprising a polymer layer disposed about the distal section of the elongate core member.

5. The guidewire of claim 4 wherein the polymer layer is selected from a group consisting of polyurethanes, polyamide, copolymers of polyurethane and copolymers of polyamide.

6. A guidewire comprising:
   an elongate core member having a proximal section and a distal section with a longitudinal portion which tapers distally to a reduced transverse dimension wherein the taper creates a substantially linear change in stiffness of the core member over a length thereof; and
   a flexible body disposed about the distal section of the core member comprising a polymer layer disposed about a radiopaque layer.

7. The guidewire of claim 6 wherein the flexible body disposed about the distal section of the core member comprises a first polymer layer disposed about the distal section, a radiopaque layer disposed about the first polymer layer and a second polymer layer disposed about the radiopaque layer.

8. The guidewire of claim 6 wherein said radiopaque layer is continuous in an axial direction.

9. The guidewire of claim 8 wherein the radiopaque layer is shorter in an axial direction than the flexible body.

10. The guidewire of claim 6 wherein the radiopaque layer is intermittent in an axial direction.

11. The guidewire of claim 10 wherein the intermittent radiopaque layer is comprised of radiopaque bands spaced apart a predetermined axial distance.

12. The guidewire of claim 11 wherein the radiopaque bands are spaced from about 0.2 to about 2 cm apart in an axial direction.

13. The guidewire of claim 11 wherein the radiopaque bands are spaced about 0.8 to about 1.2 cm apart in an axial direction.

14. The guidewire of claim 11 wherein the radiopaque bands are about 0.5 to about 5 mm in width.

15. The guidewire of claim 11 wherein the bands are about 1 to 2 mm in width.

16. The guidewire of claim 6 wherein the radiopaque layer is comprised of a radiopaque helical ribbon coil in an axial direction.

17. The guidewire of claim 16 wherein the radiopaque helical ribbon coil material is about 0.0005 to about 0.0040 inch in thickness.

18. The guidewire of claim 16 wherein the radiopaque helical ribbon coil material is about 0.5 to 2 mm in width and the turns of the radiopaque helical ribbon coil are about 1 to about 15 mm apart.

19. The guidewire of claim 6 wherein the polymer layer is comprised of a material selected from a group consisting of polyurethanes, polyamide, copolymers of polyurethane and copolymers of polyamide.

20. The guidewire of claim 6 wherein the radiopaque layer is comprised of a material selected from a group consisting of platinum, gold, iridium, palladium, tantalum, tungsten, and radiopaque alloys thereof.

21. The guidewire of claim 6 wherein the radiopaque layer is non-metallic.

22. The guidewire of claim 6 wherein the radiopaque layer comprises a polymer doped with a radiopaque material.

23. The guidewire of claim 6 wherein the polymer layer is about 0.0005 inch to about 0.0060 inch in thickness.

24. The guidewire of claim 23 wherein the polymer layer is about 0.0010 inch to about 0.0030 inch in thickness.

25. The guidewire of claim 6 wherein the radiopaque layer is about 0.0005 inch to about 0.0040 inch in thickness.

26. The guidewire of claim 25 wherein the radiopaque layer is about 0.0015 inch to about 0.0025 inch in thickness.

27. A guidewire comprising:
   an elongate core member having a proximal section and a distal section with a longitudinal portion which tapers distally to a reduced transverse dimension, wherein the tapered longitudinal portion includes a linear change in stiffness; and
   a flexible body disposed about the distal section of the core member including a polymer layer disposed about a radiopaque layer.

* * * * *